United States Patent [19]

Hodson et al.

[11] Patent Number: 5,619,984
[45] Date of Patent: Apr. 15, 1997

[54] DRY POWDER INHALATION DEVICE HAVING A POWDER-LOADED ELONGATE CARRIER

[75] Inventors: Peter D. Hodson; David K. Smith; David J. Velasquez; Anthony C. L. Wass, all of St. Paul, Minn.

[73] Assignee: Astra Aktiebolag, Sodertalje, Sweden

[21] Appl. No.: 437,291

[22] Filed: May 8, 1995

Related U.S. Application Data

[63] Continuation of Ser. No. 103,411, Aug. 6, 1993, which is a continuation of Ser. No. 933,882, Aug. 21, 1992, abandoned, which is a continuation of Ser. No. 516,328, Apr. 30, 1990, abandoned.

[30] Foreign Application Priority Data

Apr. 28, 1989 [GB] United Kingdom .................. 8909891

[51] Int. Cl.⁶ ........................ A61M 15/00; A61M 16/00; B05D 7/14; B65D 83/06
[52] U.S. Cl. .................. 128/203.15; 128/203.12
[58] Field of Search ..................... 128/203.12, 203.15, 128/203.21; 604/56

[56] References Cited

U.S. PATENT DOCUMENTS

| | | |
|---|---|---|
| 3,948,264 | 4/1976 | Wilke et al. . |
| 3,971,377 | 7/1976 | Damani . |
| 4,147,166 | 4/1979 | Hansen . |
| 4,735,358 | 4/1988 | Morita et al. . |
| 4,984,158 | 1/1991 | Hillsman .......................... 364/413.04 |
| 5,019,974 | 5/1991 | Beckers ............................ 364/413.02 |
| 5,036,462 | 7/1991 | Kaufman et al. .................. 364/413.01 |
| 5,153,827 | 10/1992 | Coutre et al. ...................... 364/413.02 |
| 5,204,113 | 4/1993 | Hartley et al. . |

FOREIGN PATENT DOCUMENTS

| | | |
|---|---|---|
| 042468A1 | 12/1981 | European Pat. Off. . |
| 069715A1 | 1/1983 | European Pat. Off. . |
| 079478A1 | 5/1983 | European Pat. Off. . |
| 166294A3 | 1/1986 | European Pat. Off. . |
| 224335A2 | 6/1987 | European Pat. Off. . |
| 239802A3 | 10/1987 | European Pat. Off. . |
| 342859A2 | 11/1989 | European Pat. Off. . |
| 403294A1 | 12/1990 | European Pat. Off. . |
| 469814A1 | 2/1992 | European Pat. Off. ............... 424/45 |
| 526166A2 | 2/1993 | European Pat. Off. . |
| 2516387 | 5/1983 | France . |
| 2346730B2 | 4/1975 | Germany . |
| 2837040 | 2/1980 | Germany . |
| 25422 | 1/1984 | Germany . |
| 8806288 | 10/1988 | Germany . |
| 432054 | 3/1984 | Sweden . |
| 1479283 | 7/1977 | United Kingdom . |
| 2061735 | 5/1981 | United Kingdom . |
| 2102295 | 2/1983 | United Kingdom . |
| 2108390 | 5/1983 | United Kingdom . |
| 2122903 | 1/1984 | United Kingdom . |
| 2144997 | 3/1985 | United Kingdom . |
| 2162152 | 1/1986 | United Kingdom . |
| 2166957 | 5/1986 | United Kingdom . |
| 2218831 | 11/1989 | United Kingdom . |
| 85/01880 | 5/1985 | WIPO . |
| 90/13328 | 11/1990 | WIPO ............................. 128/203.15 |
| 92/05824 | 4/1992 | WIPO ............................. 128/203.15 |
| WO92/15353 | 9/1992 | WIPO . |
| WO93/00951 | 1/1993 | WIPO . |
| WO93/12823 | 7/1993 | WIPO . |

*Primary Examiner*—Kimberly L. Asher
*Attorney, Agent, or Firm*—Fish & Richardson P.C.

[57] ABSTRACT

A dry powder inhalation device comprising a housing defining a chamber in communication with a patient port in the form of a mouthpiece or nasal adaptor, and an elongate carrier bearing a powdered medicament, the device being constructed and arranged such that areas of predetermined size of the elongate carrier may sequentially be exposed within the chamber, the device comprising one or more air inlets such that when a patient inhales through the patient port an air flow is established from the air inlet(s) to the patient port through the chamber such that particles of the powdered medicament of respirable size from said exposed area of the elongate carrier are entrained within the air flow.

21 Claims, 24 Drawing Sheets

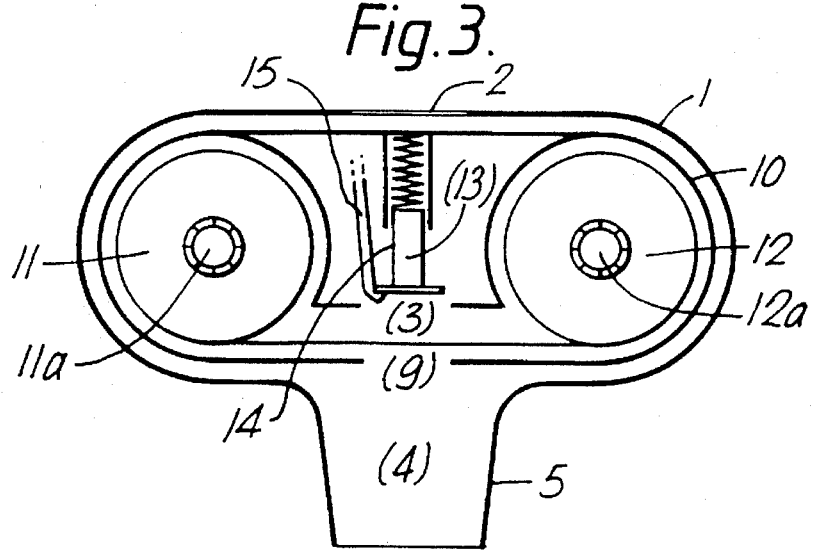
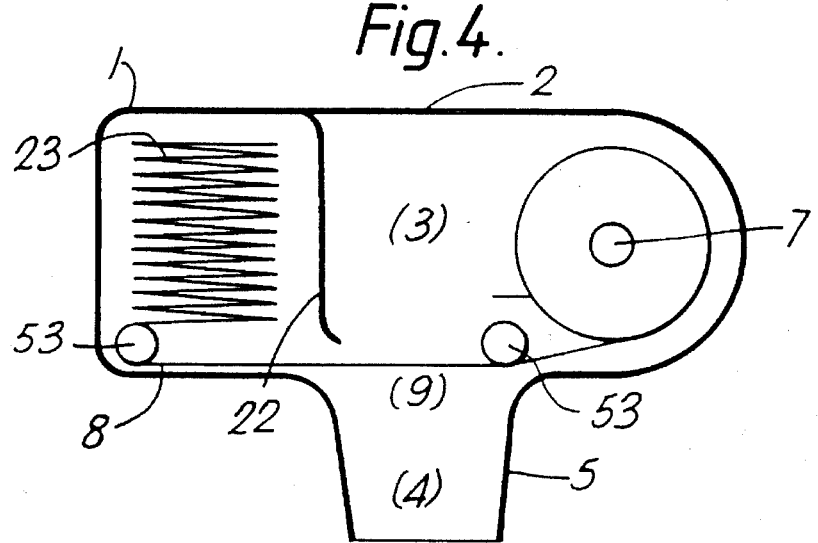
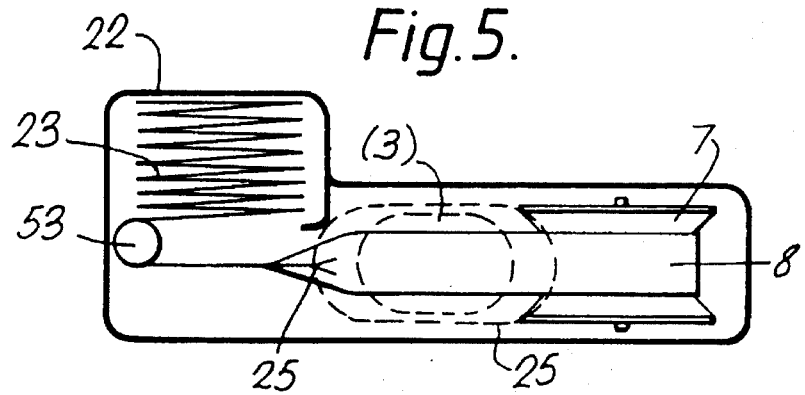

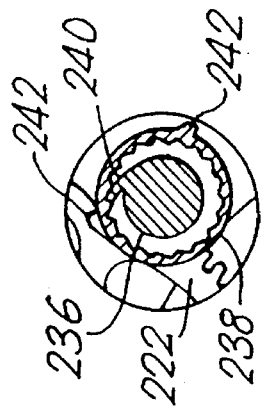
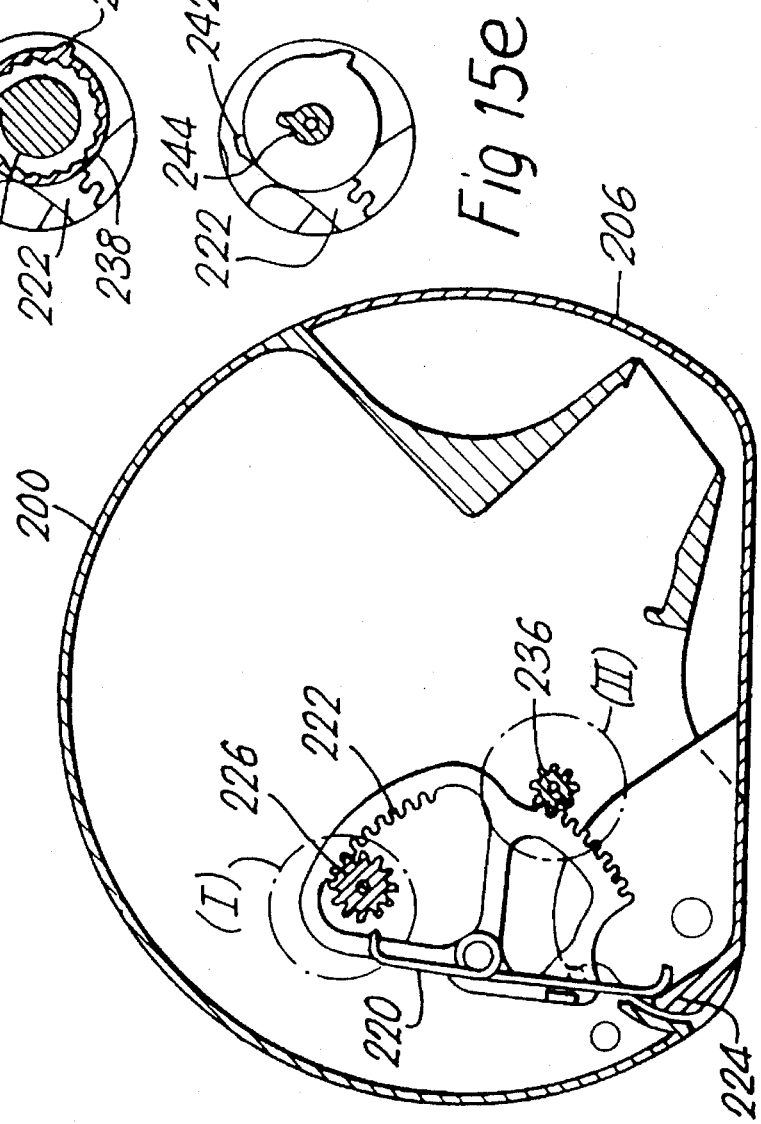
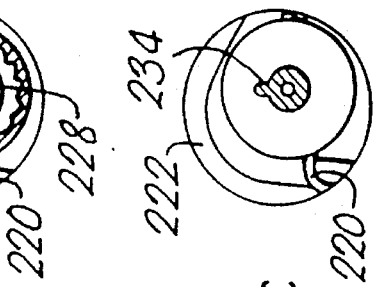
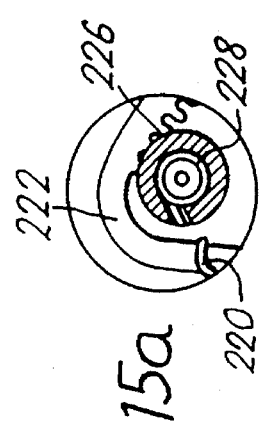

DRY POWDER INHALATION DEVICE HAVING A POWDER-LOADED ELONGATE CARRIER

This is a continuation of copending application Ser. No. 08/103,411, filed Aug. 6, 1993, (pending) which was a continuation of Ser. No. 07/933,882, filed Aug. 21, 1992 and now abandoned, which was a continuation of Ser. No. 07/516,328, filed Apr. 30, 1990 and now abandoned.

BACKGROUND OF THE INVENTION

This invention relates to a dry powder inhalation device and in particular to an inhalation device capable of dispensing a plurality of doses of medicament to a patient. The invention also relates to an elongate carrier releasably supporting powdered medicament.

Asthma and other respiratory diseases have long been treated by the inhalation of appropriate medicament. For many years the two most widely used and convenient choices of treatment have been the inhalation of medicament from a drug solution or suspension in a metered dose pressurised inhaler (MDI), or inhalation of powdered drug generally admixed with an expipient, from a dry powder inhaler (DPI). With growing concern being voiced over the strong link between depletion of the earth's ozone layer and chlorofluorocarbon (CFC) emissions, the use of these materials in pressurised inhalers is being questioned and interest in DPI systems has been stimulated.

Existing single and multiple dose dry powder inhalers use either individual pre-measured doses or bulk powder reservoirs. In both cases only fairly large quantities (e.g. several hundred micrograms) can constitute a dose due to problems associated with accurately transferring a measured small quantity of powder either into a capsule etc., or from a bulk reservoir within an inhaler. With potent drugs this introduces the necessity to add exipients, such as lactose powder, to increase the quantity of powder to be measured. These exipients are undesirable, however, as they pose subsequent powder deagglomeration problems and cause dryness in the patient's mouth. In addition, the use of individual pre-measured doses tends to lead to the production of bulky inhalation devices.

Dry powder inhalers in which the medicament is introduced into the device from a capsule are disclosed in U.S. Pat. Nos. 3,948,264, 3,971,377 and 4,147,166 and British Patent No. 1479283. Dry powder inhalers having a reservoir of dry powder from which unit doses are transferred to a chamber by means of a delivery system, such as a rotating perforated membrane in which the perforations are filled with powder from the reservoir, are disclosed in British Patent Application Nos. 2102295 and 2144997 and European Patent Application Nos. 69715, 79478 and 166294.

U.S. Pat. No. 4,735,358, European Patent Application No. 239802 and British Patent Application Nos. 2108390, 2122903 and 2166957 disclose vaporisers in which active substances capable of modifying the local atmosphere e.g. insecticides, deodorants and aromatics are vaporised for dispersion to the atmosphere. The active substance is carried or impregnated on a belt or tape consisting of a suitable base material, in such a state that vaporisation can be conducted at ambient temperature or under administration of localised heating by a vaporising head. The substance is maintained in an inactive condition until the belt passes over the vaporising head whereby thermal release is achieved. The belt may be moved to the vaporising head by hand or at a fixed speed by a motor driving feed means through a reduction gear and is taken up by a shaft or spindle. In one embodiment the belt is contained in a cassette to provide a re-usable device, the cassette being engaged by drive means and having a suitable aperture for the belt to pass across the vaporising head. None of the vaporisers disclosed are suitable for delivering a predetermined unit dose of powdered solid medicament to a patient.

SUMMARY OF THE INVENTION

It has now been found that predetermined doses of a dry powder may be stored in and dispersed from an inhaler by means of a preloaded elongate carrier, such as a tape or cord.

Therefore according to the present invention there is provided a dry powder inhalation device comprising a housing defining a chamber in communication with a patient port in the form of a mouthpiece or nasal adaptor, and an elongate carrier bearing a powdered medicament, the device being constructed and arranged such that areas of predetermined size of the elongate carrier may sequentially be exposed within the chamber, the device comprising one or more air inlets such that when a patient inhales through the patient port an air flow is established from the air inlet(s) to the patient port through the chamber such that particles of the powdered medicament of respirable size from said exposed area of the elongate carrier are entrained within the air flow.

The invention provides a simple, effective dry powder inhaler which is capable of delivering multiple, uniform doses of a medicament to a patient. The device is simple to operate and does not require the patient to insert capsules of medicament or rely upon a separate reservoir of medicament in order to load the device for use. The medicament is generally preloaded on an elongate carrier, sections of which are sequentially exposed in the chamber for dispensing the medicament. The elongate carrier may be conveniently loaded on a spool (in a similar manner to a photographic film) or in a cassette (in a similar manner to an audio cassette). The elongate carrier may have any ratio of length:width but is generally greater than 5:1, usually greater than 10:1 preferably between 100:1 and 1000:1.

The preloaded elongate carrier can take a variety of forms, but preferably is a tape, web, belt or cord. The powdered medicament may be retained on the carrier by electrostatic attraction, van der Waals forces, physical attraction, mechanical binding, wedging or by a cover layer or an overlying layer of the same carrier when the carrier is wound etc. One or more surfaces of the carrier and optionally the interior of the carrier may be configured to assist in retaining the particles of powder.

The carrier may be constructed from one or more of a wide range of natural and synthetic materials e.g. polyethylene, polypropylene, polyester, polytetrafluoroethylene or a co-polymer thereof and cellulose. The materials may be in the form of non-woven fibrous materials, loose weave materials or fabrics, materials having a surface pile, films, microporous materials, microgrooved materials, cords of twisted fibres, or any material or composite of more than one material having small surface grooves, recesses, interstices, apertures or embossed surface structures having a typical size of <500 μm in either depth or height and of greater than 0.1 μm in at least one other dimension in order to retain the particles of powder.

A microgrooved material preferably comprises a tape, web or belt with one or more grooves of width 10 to 500 μm at the carrier surface and a depth of 10 to 500 μm, but the grooves may generally have dimensions at least an order of magnitude larger than the largest particle. The microgrooves may be filled partially, or completely, the latter facilitating a means of dosage control if the material is loaded under uniform conditions. The microgrooves need not be continuous or straight and may run in one or two dimensions.

A microporous material preferably comprises a tape, web or belt having pores of diameter 0.1 to 100 μm which may be randomly orientated. At least a portion of the pores must be on the exterior surface. A preferred method of pore formation utilises solvent extraction of oil droplets dispersed in a film of carrier material.

A further embodiment of a microporous material is produced by a laser drilling process and comprises a tape, web or belt having pores of diameter 1 to 100 μm, preferably 20 to 50 μm, in at least one surface.

A non-woven material may be of any suitable format, but is preferably in the form of a tape, web or belt. It may contain any type and form of fibres, although fibres of 0.1 μm to 100 μm diameter are preferred and most preferably 5 to 20 μm diameter. Fibres may be of any appropriate length but preferably 1 to 100 mm. Formation of the non-woven material may be any suitable method, for example, combing or carding, deposition of fibres from a transport gas or fluid, or the extrusion and blowing of microfibres. Bonding, e.g. by thermal fusion, of the fibres over at least part of the area of the material may be carried out to increase the mechanical strength of the material. Such bonding may be most conveniently situated at the edges of the tape or web and may be conveniently formed as part of a process of slitting the tape, e.g., by a thermal or laser slitting means. The material may also be perforated or embossed and may optionally be air permeable.

The non-woven material may use a mixture of fibre compositions or forms. In one preferred embodiment, bicomponent fibres, with a readily-fusible outer component, are used. Such fibres are capable of ready inter-bonding to prevent, or minimise fibre shedding. In another preferred embodiment, spun-bonded fibres are used to achieve the same objective by taking advantage of their longer fibre length. In a third embodiment, continuous reinforcing filaments may lie in the plane of the material, so providing fibre anchorage and conferring additional mechanical strength to the material. In a fourth embodiment, paper type non-woven materials formed by deposition of fibres from a liquid may be used, as they may possess additional strength compared to other materials and may lead to reduced fibre shedding, due to increased fibre entanglement.

The tape, web or belt may contain reinforcing threads in the plane of the material and/or a backing layer e.g. a metal foil such as aluminium, or a polymer film or a combination thereof. A metallized backing layer is advantageous when the carrier is stored as a roll because it imparts a conducting surface, which may reduce transfer of medicament from the coated surface to the uncoated surfaces. The backing layer may have perforations to allow for passage of an airflow through the carrier material proper.

The carrier may be loaded by the brushing, scraping or smearing of powdered medicament onto the carrier surface.

Alternatively the carrier may be loaded by evaporation from a suspension of medicament, by precipitation from a solution of medicament or by deposition from an aerosol for example by spraying, impaction, impingement, diffusion or by electrostatic or van der Waals attractions. For example, the medicament particles may be given an intentional electrical charge immediately prior to loading. The technique of charged aerosol deposition may be complimented by the use of a carrier with an inherent electrostatic charge. Ideally, the carrier should be an insulator such as polytetrafluoroethylene capable of retaining the charge, alternatively the carrier may contain an artificial charge due to the presence of electrets. Generally, the choice of loading technique will be governed by the properties of the carrier material employed.

Masks stencils etc. may be employed during coating, in order to allow the coating of discrete areas of carrier medium with individual doses. Patterned deposition of the medicament may be used to prevent contact between drug and any ink markings on tape.

A preferred carrier for use in this invention is disclosed and claimed in U.S. Patent Application Number, Attorney Docket FN 45128 U.S.A. 1A, of even date incorporated herein by reference. That Patent Application discloses a flexible sheet material comprising a plurality of discrete depressions in at least one surface thereof, each of the depressions having a depth of about 5 to 500 μm, but less than the thickness of the sheet material, and an opening at the surface of the sheet material of about 10 to 500 μm across, a substantial number of the depressions being at least partially filled, preferably at least 75% filled, with micronised medicament, and the area of the surface of the sheet material between the depressions being substantially free of micronised medicament.

The flexible sheet material may comprise a substantially regular array of depressions or microdimples formed in the top surface of a layer of polymeric material. The depressions are generally truncated cones, but may alternatively be of any suitable configuration for holding micronised medicament including generally truncated pyramids, partial hemispheres and tetrahedrons and other geometric configurations, as well as non-geometrical configurations. Presently preferred depressions have a sidewall angle of about 15° to 20° to the vertical. The array of depressions may take any form or pattern and need not be regular (i.e., the array may be irregular in appearance).

The depressions generally have a depth of about 5 to 500 μm and an opening at the surface of the sheet material of about 10 to 500 μm across with respect to the major axis of the opening. In the case of the depressions having generally circular openings such as truncated cones or partial hemispheres, for example, the major axis discussed above is, in fact, the diameter of the circular opening. Preferred depressions have a depth of about 5 to 150 μm and an opening (e.g., diameter in the case of truncated cones or partial hemispheres or the like) at the surface of the sheet material of about 50 to 200 μm. The depressions generally will be spaced about 20 to 200 μm, preferably about 50 to 200 μm, from one another. Preferably the depressions will number from about 500 to 15,000 per $cm^2$ of the sheet material. The volume of each depression and the spacing or number of the depressions will depend upon the potency of the medicament and the area of the sheet material intended to represent a single dose of the medicament. Preferably, the sheet material will have a substantially uniform depression volume per unit area.

The sheet material may further comprise a support layer, e.g., of paper. The layer of polymeric material may be laminated or melt-bonded to or extruded onto the support layer. Other support layers may be formed of non-wovens or polymers such as polyester.

The layer of polymeric material may comprise any suitable polymer such as polyethylene, polypropylene, polyester, polytetrafluoroethylene and cellulose. Polyethylene is preferred. The layer of polymeric material will be typically about 25 to 1000 μm in thickness.

The sheet material may be formed of a single material such as polypropylene. The support layer is not required in such an embodiment since the sheet material even without the support layer will exhibit sufficient integrity and durability.

A preferred sheet material is prepared using polyethylene-coated kraft paper available from Schoeller Company. The depressions have a depth such that they do not form pores extending through the entire thickness of the sheet material.

The top surface of the sheet material is generally coated with micronised drugs to at least partially fill the depressions followed by general removal of excess drug from the top surface of the sheet material in the areas of the top surface between the depressions, e.g., by scraping optionally followed by rolling between silicone pads, silicone having an affinity for the particles of drug.

As the packing density of the micronised medicament in the depressions may have influence on the form and amount of medicament released from the sheet material during the aerosolisation process, care should be taken to assure that the packing density remains substantially uniform during the coating process.

The opening and depth dimensions and the spacing of the depressions influence how much micronised medicament the sheet material can carry per unit area for a given degree of compression of the medicament during loading or coating. Further, depression depth may influence the degree to which medicament is released from the sheet material and its relative state of agglomeration or unagglomeration. Using albuterol sulfate with a mean particle size of 1.7 μm and for single impactions of strength appropriate to an inhaler on areas of about 2 to 10 cm$^2$ of sheet material, the following was observed. The percentage of medicament retained on the sheet material or tape decreases as depression depth increases, this being about 95% at 14 μm, about 60% at 28 μm and about 35% at 45 μm. Further, the respirable fraction (i.e., the percentage of drug which is in particles of aerodynamic diameter of equal to or less than about 6.4 μm) similarly decreases as depression depth increases, this being about 65% at 14 μm, about 30% at 28 μm and about 10% at 37 μm. These two trends result in the proportion of total medicament released in particles of respirable size remaining generally similar for the depression depths studied (this being about 5 to 15% of total medicament).

Depressions may be formed in the sheet material by any suitable technique such as micro-imprinting using a photo-lithographically-patterned magnesium alloy plate orother micro-machined plate. Other conventional techniques which may be used are optical imaging or laser imaging.

As an illustrative example a sheet material has been prepared using a photolithographically produced etched magnesium alloy master plate having an array of pyramidal-shaped protuberances numbering about 1550 per cm$^2$ wound about a steel roller. The roller was heated to about 225° F. using oil. The polyethylene surface of polyethylene-coated kraft paper (commercially available from Schoeller Company) was pressed against the surface with a rubber or steel nip roll, also heated with oil and hydraulically pressurised against the patterned roll.

It is preferred that the medicament employed exhibit a potency which permits a single dose to be loaded onto the sheet material in an area of less than about 25 cm$^2$ and preferably less than about 5 cm$^2$. More preferred is a sheet material containing a drug in such a manner and of such a type that between 0.25 and 2.25 cm$^2$, most preferably between 0.5 and 2.0 cm$^2$ of the sheet material will contain a single dose. Stated differently, given that a sheet material of the invention may conveniently carry between about 10 and 150 μg of medicament per cm$^2$, the potency of the medicament will preferably be such that a single dose may be carried on the above stated 0.25 to 2.25 cm$^2$ of sheet material.

The format of the carrier in the most preferred embodiment is a tape. The nature of the carrier dictates the method of transport between storage means and the chamber where aerosolisation takes place. In a preferred embodiment, storage of preloaded carrier is effected by winding on a spool which is contained within a cassette. Use of a tape web or belt allows other conformations to be imparted to the stored carrier by folding, for example, as a concertina conformation which has the advantage that the medicament bearing surfaces are in association and thereby prevent net transfer of medicament during storage. Each fold may define a unit dose of medicament. Folding along the longitudinal axis of the tape, referred to as hybrid folding, may also reduce unwanted net transfer of medicament. Cord or string may conveniently be stored as a coil.

The device includes means for advancing the elongate carrier through the chamber to sequentially expose areas of the carrier for release of medicament during inhalation by the patient. The means for advancement may take a variety of forms depending upon the type of elongate carrier and whether the exposed areas of carrier are to be retained within the device. For example, tapes webs and belts may include a series of apertures which are engaged by one or more sprocketed guide wheels or rollers in a similar manner to a camera or printer. Alternatively, or in addition, the carrier may be wound on a take-up spool, rotation of the spool directly or via a drive belt causing the carrier to advance. The device may also include means for tensioning or otherwise maintaining the exposed area of the carrier within the chamber during inhalation by the patient.

The elongate carrier may be advanced into the chamber prior to inhalation by the patient preferably or the carrier may be advanced into the aerosolisation chamber during inhalation to protect the powdered medicament from premature exposure. For example in one embodiment of the inhaler an unexposed area of carrier is rapidly advanced into the chamber upon actuation, and is rapidly decelerated or brought to an abrupt halt and preferably is impacted thereby imparting sufficient energy to the medicament particles to effect their displacement from the carrier into the air stream.

In the preferred embodiment of the invention the elongate carrier is stored in a cassette both before and after exposure. The cassette may comprise one or preferably two spools together with idlers or other rollers and include an exposure frame positioned within the chamber, through which the carrier is advanced. The cassette may be removable to allow the device to be recharged with a new cassette. However, it is not essential for the exposed areas of the carrier to be retained within the device and spent carrier may be advanced to the exterior of the device through a slot in the housing whereupon disposal may be effected by the patient, optionally with the aid of a cutting edge. This arrangement is particularly suitable for a tape carrier which has transverse perforations to facilitate tearing off spent carrier.

The device preferably additionally comprises means for releasing medicament of respirable size from the exposed area of carrier independent of the patients' inspiratory effort.

The medicament release means overcomes the binding of the medicament particles to the carrier by mechanical effort e.g. impaction, vibrations, gas flow etc. or electrostatically. Mechanical energy input may be achieved by:

- impaction means e.g. one or more spring biased striking hammers having one or more impactions upon the exposed section of carrier;
- brushing or scraping means having rotary or reciprocal motion upon the exposed section of carrier e.g. spring charged or electrically driven rotary elements having projecting bristles or flaps; dragging the carrier across irregularities such as a serrated idler wheel or a surface bearing a plurality of embossed structures or similar surface features;
- pressurized gas flowing past, through or impinging upon the carrier, emanating from some compressed or liquefied gas supply;
- vibration means for imparting vibration to the exposed section of carrier, generally in the frequency range 5 to 50,000 Hertz; the vibrations may be derived electrically or piezoelectrically e.g. using the piezoelectrical properties of polymer $PVDF_2$; electromagnetically e.g. use of an electromagnetic vibrating arm or pin; or mechanically e.g. use of rotating cams or serrated wheels, which may involve rapid revolution of the cam or wheel in contact with the carrier or movement of the carrier across the cam or wheel.

In a further embodiment vibration means may comprise means for the rapid acceleration of the elongate carrier, preferably from an unexposed storage state, into the chamber followed by a sudden and rapid deceleration preferably to a dead stop to facilitate medicament release. In such an arrangement the particles of medicament are given sufficient kinetic energy such that they are released from the carrier when the carrier comes to a rapid halt. In a further embodiment the elongate carrier is maintained as a slackened loop following advancement into the chamber. Upon actuation tensioning means effect a sudden and rapid straightening of the carrier loop causing particles of medicament to be displaced. The loop may be positioned in any orientation relative to the patient port but in a preferred embodiment the centre of curvature of the loop is positioned between the carrier and patient port so that the particles of medicament are released towards the patient port when the loop is rapidly straightened.

Medicament release efficiency may be increased when the carrier and/or the medicament particles have an intentional charge by reversing the polarity of the carrier at aerosolisation and inhalation.

The means for releasing medicament from the carrier during inhalation is preferably triggered in response to the patient inhaling in order to avoid the patient having to synchronise inhalation and actuation of the release mechanism. Airflow detection may conveniently be accomplished by means of a movable vane positioned within the chamber or patient port, motion of the vane causing actuation of the release mechanism. Such a vane may also be constructed to prevent a patient exhaling through the device and/or preventing exhaled air from reaching the stored carrier thereby avoiding any problems associated with moisture. Other such sealing means may also be employed. A suitable desiccant cartridge may be incorporated into the inhaler or may be incorporated into the carrier cassette.

Suitable medicaments for use in the invention include any drug or drugs which may be administered by inhalation which is a solid or may be incorporated in a solid carrier. Suitable drugs include those for the treatment of respiratory disorders e.g. bronchodilators, corticosteroids and drugs for the prophylaxis of asthma. Other drugs such as anorectics, anti-depressants, anti-hypertensive agents, anti-neoplastic agents, anti-cholinergic agents, dopaminergic agents, narcotic analgesics, beta-adrenergic blocking agents, prostoglandins, sympathomimetics, tranquillisers, steroids, proteins, peptides, vitamins and sex hormones may be employed.

Exemplary drugs include:

Salbutamol, Terbutaline, Rimiterol, Fenoterol, Pirbuterol, Reproterol, Adrenaline, Isoprenaline, Ociprenaline, Ipratropium, Beclomethasone, Betamethasone, Budesonide, Disodium Cromoglycate, Nedocromil Sodium, Ergotamine, Salmeterol, Fluticasone, Formoterol, Insulin, Atropine, Prednisolone, Benzphetamine, Chlorphentermine, Amitriptyline, Imipramine, Clonidine, Actinomycin C, Bromocriptine, Buprenorphine, Propranolol, Lacicortone, Hydrocortisone, Fluocinolone, Triamcinclone, Dinoprost, Xylometazoline, Diazepam, Lorazepam, Folic acid, Nicotinamide, Clenbuterol, Bitolterol, Ethinyloestradiol, Levonorgestrel and pharmaceutically acceptable salts thereof.

The powdered medicament may be finely micronised by repeated step wise millings or a closed loop milling system and preferably is in the particle size range of 1 to 10 μm. The medicament may comprise one or more drugs, having one or more particulate forms and may include one or more physiologically acceptable or inert exipients. The medicament particles may possess a coating comprising a surfactant, such as a perfluorinated surfactant or other surfactants such as Span 85, oleic acid, lecithins.

The predetermined area of carrier to be exposed in the chamber may be from 0.1 to 20 $cm^2$ and preferably from 1 to 5 $cm^2$ e.g. 2 to 3 $cm^2$. The medicament may coat one or more surfaces of the carrier and/or be entrapped within recesses or interstices in the carrier to allow a dose of 5 μg to 1 mg to be entrained within the airflow produced at inhalation. It is not essential that all of the drug be entrained within the airflow providing the amount of drug released from the predetermined area is substantially reproducible when the device is used.

The device of the invention may incorporate means to indicate one or more of a variety of parameters, such as, readiness for use, contents remaining, type of drug etc.

The indicator may just provide warning of the near-exhaustion of the medicament supply or may provide more detailed information, such as the sequential number of the dose or the number of doses left. The indicator may provide information of the date of manufacture or date of expiry of the medicament, as additional examples. For treatment intended to be taken regularly at set times, the indicator may display the intended day, date and time of administration. The information displayed by the indicator may conveniently be marked on the tape or tape covering by any appropriate method, whether involving printing, indenting etc. The area of tape in the indicator need not be that used to release the drug at that time. The indicator may be of an extremely simple form, such as a window or aperture to reveal the amount of elongate carrier remaining on the supply spool of a cassette, the window being visible externally or when a cover is opened to expose the cassette within the device.

The device may incorporate means to vary the area of elongate carrier exposed in the chamber thereby providing a variable dose facility. For example, an internal cover for the elongate carrier may be provided which is movable to expose varying lengths of carrier to the chamber. Alternatively, or additionally, rollers supporting the exposed length of the carrier may be movable to vary the distance between the rollers thereby altering the exposed length of the carrier.

The devices of the invention may possess numerous advantages over the prior art devices. For example:

1. An inhaler with dosage control by the removal of powder from a fixed area of uniformly coated tape may show improved dose uniformity and respirable fraction uniformity over prior art devices. High respirable fractions are desirable because they allow a high proportion of the drug to be inhaled into the lungs to provide therapeutic benefit, and reduce the proportion of the drug causing unwanted systemic side-effects following swallowing from the mouth and throat region.

2. The inhaler allows the accurate administration of smaller quantities of undiluted potent drugs (typically below 200 µg) such as corticosteriods, than is currently possible. This removes the problems associated with the use of exipients.

3. The storage of pure, powdered medicament on the surface of a tape lends itself to dosage adjustment or the use of different drugs with the minimum of effort and without reformulation work.

4. The inhaler is suitable for use with a wide variety of different medicaments.

5. By controlling the tape or web dimensions, a precise number of doses for inhalation can be stored in the inhaler.

6. The tape can be marked to allow the inhaler to register the exact number of doses remaining, or alternatively some counter mechanism can be driven by the carrier advance mechanism.

7. If indirect breath actuation is incorporated the amount of drug inhaled and the degree of particle deagglomeration are independent of the patient's inspiratory effort in the inhaler. Indirect breath-actuation can be used in this invention, offering the advantage for such devices of being able to overcome patients' hand/lung co-ordination problems, while at the same time providing a consistent dose each time for all patients, irrespective of lung function.

8. If indirect breath actuation is incorporated the deagglomeration of the drug is not dependant on air flow rate, so that patients can be taught to inhale slowly (unlike for most dry powder inhalers), thus reducing unwanted drug impaction on the back of their throats.

BRIEF DESCRIPTION OF THE DRAWINGS

The invention will now be described with reference to the accompanying drawings in which:

FIG. 3 is a section through an inhaler of the present invention having a cassette comprising spooled carrier storage and take-up means and impaction means for aerosolisation, FIG. 4 is a section through an inhaler of the present invention having concertina folded carrier storage and integral take-up spool, FIG. 5 is a section through a variant of the dry powder inhaler of FIG. 4 having hybrid folded storage in addition to concertinaed stacking of carrier, FIG. 6a is a front view, FIG. 6b a rear view and FIG. 6c a ventral view of the device exterior. FIG. 6d is a transverse section through the inhaler along the axis A—A, FIG. 7a is a front view and FIG. 7b a rear view of the device exterior. FIG. 7c is a transverse section through the inhaler along the axis B—B, FIG. 11a is a section through the device in closed format; FIG. 11b is a section through breath actuation means at patient inhalation and FIG. 11c is a section through the device in open format at medicament aerosolisation, FIGS. 13 to 29 represent cross-sections through a further device in accordance with the invention.

DETAILED DESCRIPTION OF PREFERRED EMBODIMENT

Figure 1A:
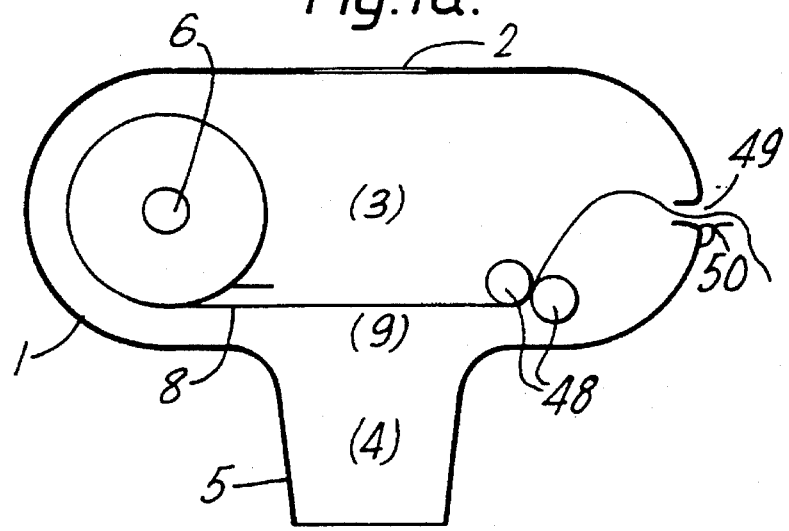
FIG. 1a is a section through an inhaler of the present invention having a single integral carrier storage spool.

Referring to FIG. 1a, an inhaler of fully disposable format is illustrated, comprising a housing (1) having integral air vents (2) and defining an aerosolisation chamber (3) in communication with a patient port (4), having a mouthpiece adaptor (5) in this embodiment. Alternatively, the device may be fitted with a nasal adaptor (not shown) or the device may be supplied with both. Within said chamber are integral carrier storage spool (6) and carrier engaging rollers (48) which may be sprocketed to engage the carrier by means of a series of apertures cut in the carrier.

Carrier (8) is sequentially advanced across the exposure frame (9) and subsequent to exposure, through slot (49) in the housing. Spent carrier may be discarded by the patient with the aid of cutting edge (50) in a process analogous to a cap gun or a tape dispenser. Dose advancement means are not shown but may comprise mounting rollers (48) on a drive shaft extending through the housing (1). This may be manually turned with the aid of a knurled knob. Alternatively a suitable gear train may be connected to roller(s) (48) and a recessed dose advancement lever or wheel mounted in the housing to effect dose advancement.

Figure 1B:
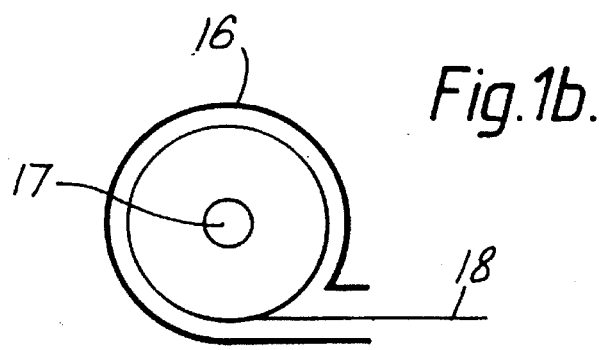
FIG. 1b is a section through a disposable cassette for an inhaler of the present invention comprising a single carrier storage spool.

FIG. 1b is a section through a cassette of preloaded carrier comprising: a cassette housing (16), a carrier storage spool (17) and free carrier leader portion (18) which is inserted into a device take-up means. Such a cassette is suitable for use in the inhaler of FIG. 1a (optionally as a re-usable device) where the cassette replaces spool (6). The leader portion upon loading would be threaded, in a manner analogous to loading a 35 mm photographic film to engage rollers (48) and protrude through slot (49). Alternatively the leader portion may be inserted into a take-up spool by means of a slot cut in said spool.

Figure 2:
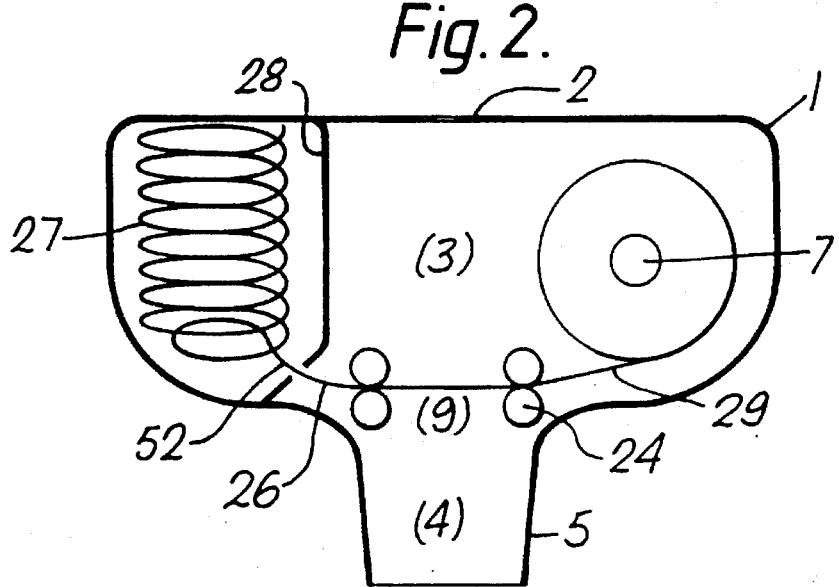
FIG. 2 is a section through an inhaler of the present invention having a carrier of cord stored as a coil and integral take-up spool.

Referring to FIG. 2, an inhaler of fully disposable format is illustrated, comprising a cord carrier (26) stored as a coil (27) in a storage compartment (28) distinct from aerosolisation chamber (3). Means for sealing stored cord from moisture ingress may be provided at opening (52). Sequential advancement of cord under tension by sprung rollers (24) to exposure frame (9) allows for aerosolisation of the medicament carried. Subsequent to exposure, spent carrier (29) is taken up by integral spool (7). Dose advancement means are not shown but may comprise a shaft continuous with the spindle of spool (7) extending through the housing and turned by means of a knurled knob, or by a suitable gear train engaging spool (7) and connected to a recessed dose advancement wheel or lever mounted in the housing.

Referring to FIG. 3, an inhaler of re-usable format is illustrated comprising a disposable cassette (10) having carrier storage spool (11) and take-up spool (12). Spools (11,12) are engaged respectively on cassette insertion by spindles (11a,12a). The embodiment depicted comprises impaction means (13) for the aerosolisation of medicament at exposure frame (9) upon release, either manually or indirectly by breath actuation means, explained hereinafter, of a spring biased hammer (14) held in an armed position (as illustrated) by catch (15). Means for arming the hammer are not shown.

An inhaler of fully disposable format is produced by replacing cassette (10) with integral spools (6) and (7).

Referring to FIG. 4, an inhaler having folding means of carrier storage is illustrated, comprising a carrier storage compartment (22), wherein carrier (8) is stored in a concertinaed configuration (23) such that medicament bearing surfaces are in association. Carrier is sequentially advanced under tension by rollers (53) which may be spring biased or sprocketed to engage the carrier in register and provide support means. Spent carrier exposed at exposure frame (9) is taken up by integral spool (7) which interacts with dose advancement means.

Referring to FIG. 5, a variant of the inhaler depicted in FIG. 4, comprising carrier (8) being folded across the longitudinal axis prior to concertina folding (23). Medicament bearing surfaces of the carrier are folded inwardly to prevent net medicament transfer and to reduce moisture ingress. Sequential advancement of carrier, by drive means associated with integral take-up spool (7) and under tension provided by roller (53), causes unfolding of carrier immediately prior to exposure at exposure frame (9). Mouthpiece (5) is depicted with dotted lines to illustrate positioning.

Figure 6A:
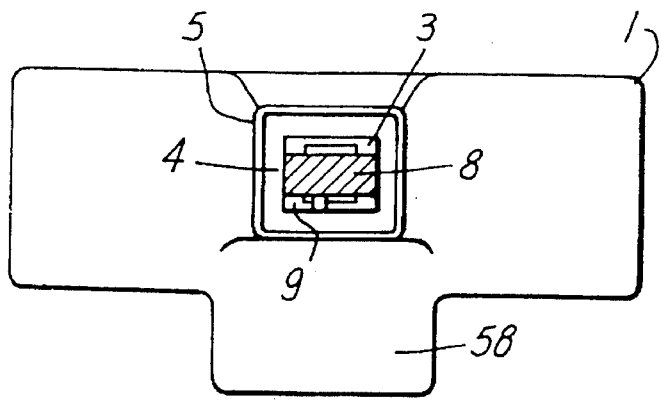
FIGS. 6a to 6d illustrate an inhaler of the present invention having indirect breath actuation, prevention of through exhalation vane and impaction means for aerosolisation.

Referring to FIG. 6a, a front view of an inhaler having indirect breath actuation of impaction means is illustrated. Vane (56), explained hereinafter is shown in the displaced position. Exposure frame (9) presented to the patient by insertion of mouthpiece (5) into the buccal cavity defines the exposed area of carrier (8). Striking hammer (14) is held in an armed position by catch (15) and is released by the detection of an air flow through the device.

Figure 6B:
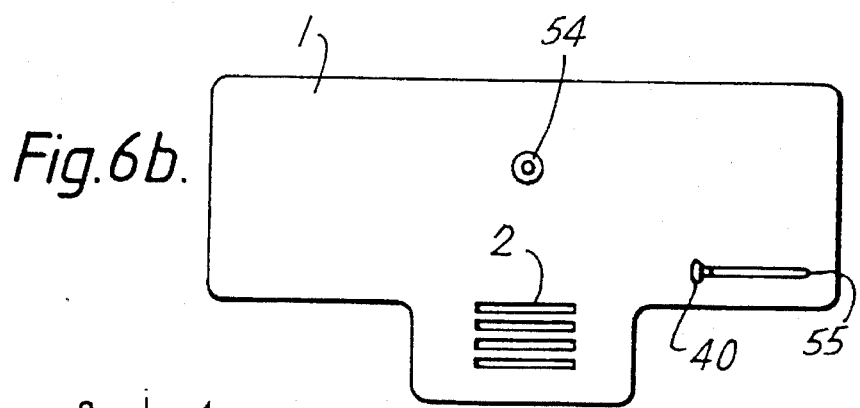

FIG. 6b depicts a rear view of the inhaler of FIG. 6a and illustrates the position of air vents (2), striking hammer arming rod (54) and dose advancement lever (40) recessed in slot (55).

Figure 6C:
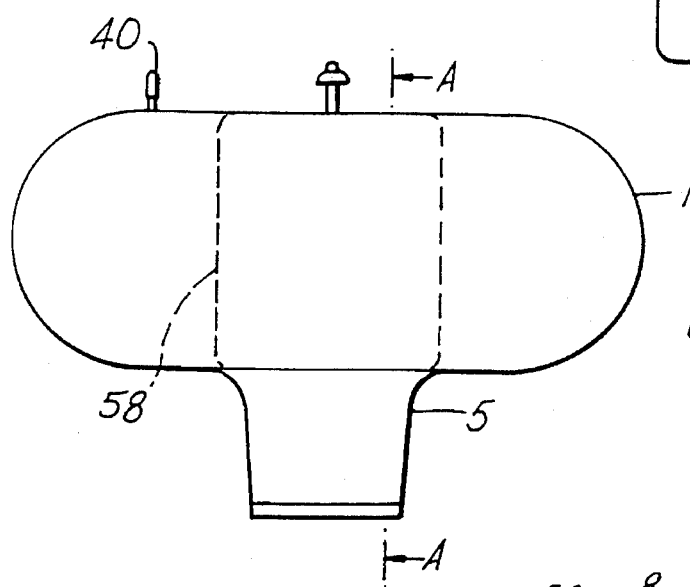

FIG. 6c depicts a ventral view of the inhaler of FIG. 6a and serves to illustrate the housing extension (58) containing indirect breath actuation means and the arming rod (54) in non-armed position flush with the housing.

Figure 6D:
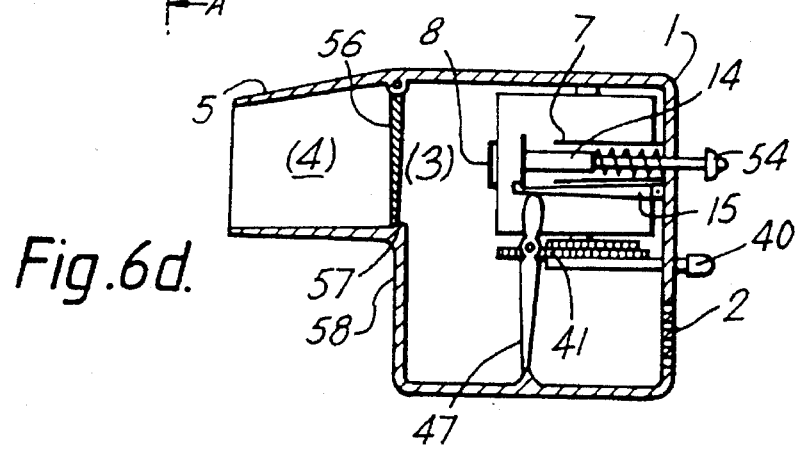

FIG. 6d depicts a section through the inhaler along the axis A—A. The inhaler comprises: a housing (1) having an extension (58), for purposes of indirect breath actuation with integral air vents (2), said housing defining an aerosolisation chamber (3) in communication with patient port (4) and air vents (2). Carrier (8) is taken up by spool (7). Carrier storage means are not shown but typically would be a spool.

Unexposed carrier (8) is sequentially advanced across exposure frame (9) by recessed lever (40) driving a suitable gear train (41) turning spool (7). Striking hammer (14) is primed by the patient immediately prior to inhalation by retracting spring biased rod (54) until catch (15) is engaged.

Vane (47) is capable of being displaced when an air flow is generated by patient inhalation through the device. The vane is spring biased (not shown) to return to the displaceable home position when the air flow is halted. Displacement of the vane (47) produces an interaction with catch (15) to release the striking hammer (14). Impaction of the hammer with carrier (8) releases medicament particles of respirable size into aerosolisation chamber (3), whereupon they are entrained into the developing air stream as the patient inspires.

Vane (56) ensures unidirectional flow of air from the exterior atmosphere, via air vents (2) to patient port (4), by being displaceable in the forward direction only. Movement in the reverse direction upon patient exhalation is prevented by stop (57).

In a modification (not shown) the vanes (47) and (56) may be replaced by a simple vane.

Figure 7A:
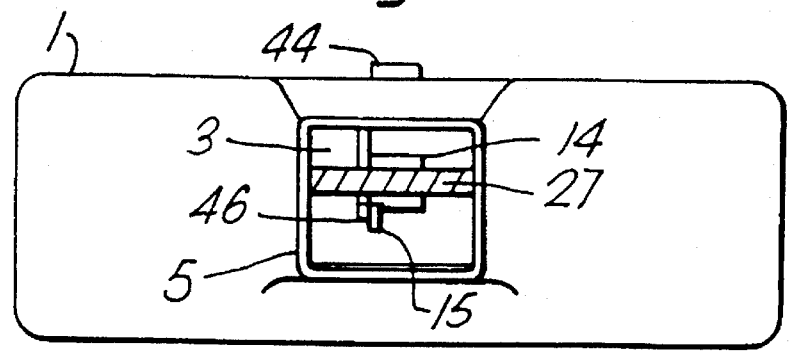
FIGS. 7a to 7c illustrate an inhaler of the present invention having manual actuation of impaction means for aerosolisation.
Figure 7B:
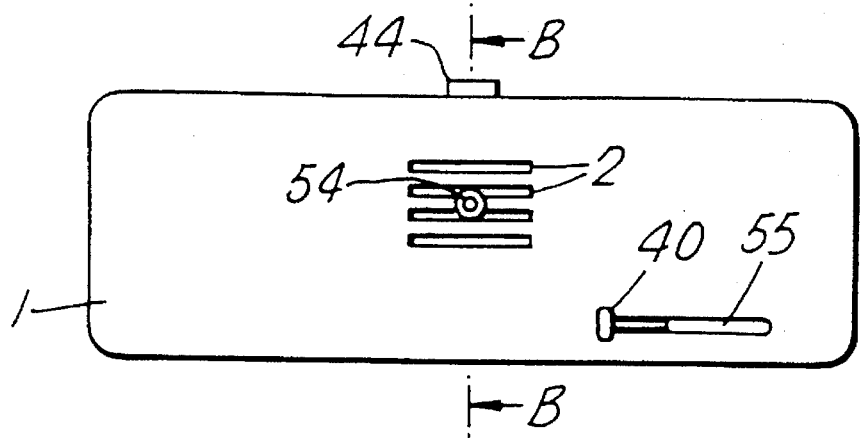
Figure 7C:
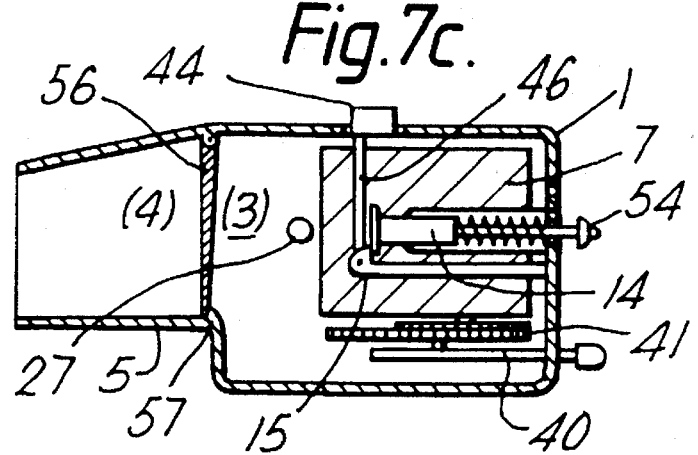

Referring to FIGS. 7a to 7c, an inhaler having a cord carrier and manually circulated impaction means for aerosolisation. Cord (27) is sequentially advanced across exposure frame (9). Rod (54) is retracted immediately prior to use until the hammer (14) engages catch (15). The patient inserts the inhaler into his oral or nasal cavity and depresses button (44) which connects with spring biased lever (46) to cause catch (15) to release the armed striking hammer. The hammer contacts the cord with sufficient energy input to aerosolise medicament particles of respirable size. Simultaneously inspiration produces an air flow through the device entraining aerosolised medicament to the patient.

Figure 8A:
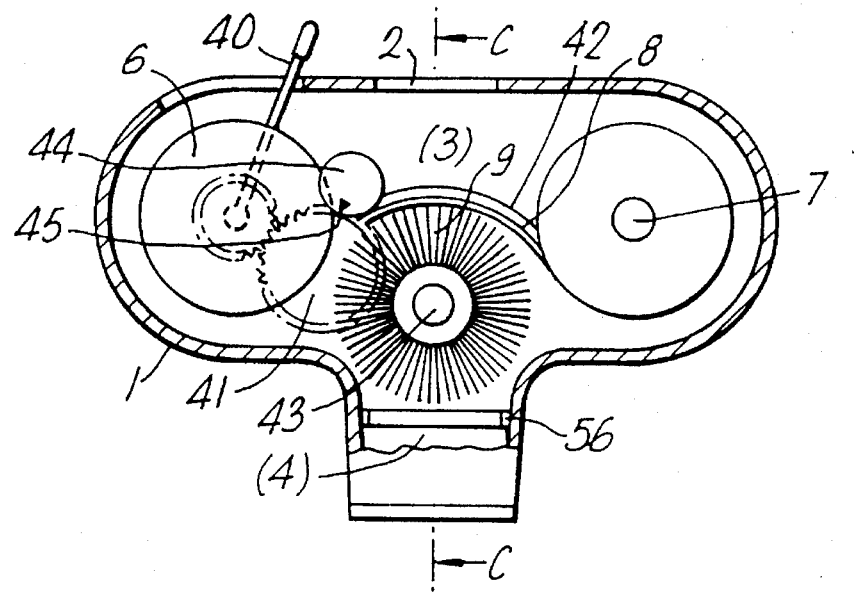
FIG. 8a is a section through an inhaler of the present invention having a revolving brush for aerosolisation of carrier borne medicament.
Figure 8B:
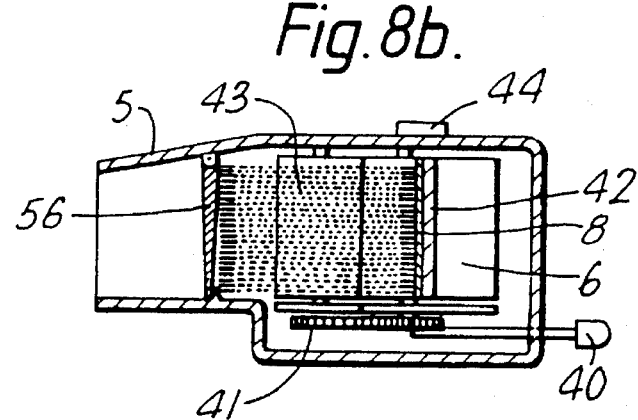
FIG. 8b is a transverse section of the inhaler in FIG. 8a along the axis C—C.
Figure 8C:
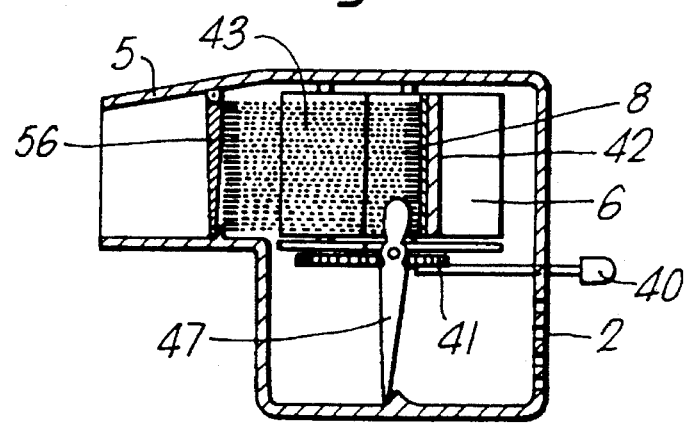
FIG. 8c is a transverse section through a variation of the inhaler illustrated in FIG. 8a having indirect breath actuation.

Referring to FIGS. 8a to 8c, an inhaler of fully disposable format having both integral spooled carrier storage (6) and take-up (7) and brushing/scraping means for aerosolisation. Carrier (8) is sequentially advanced across the carrier support (42) in contact with a spring powered or electrically driven (not shown) rotary brush (43). Contact is only made between brush filaments and carrier at the exposure frame (9). Synchronisation of brush action with exposure of a fresh section of tape is achieved by the embodiment illustrated by FIGS. 8a and 8b in which a push button (44) interacts with a spring biased check pawl (45) to prevent advancement of carrier by a recessed lever (40) and suitable gear train (41) until the button is depressed. The same push button or a different push button switch when depressed may complete a circuit comprising a battery and a motor (not shown) or allow a tensioned spring mechanism (not shown) to revolve the brush. Alternatively the gear train (41) responsible for carrier advancement may interact with the brush directly, thereby synchronising their motion.

FIG. 8c illustrates the application of indirect breath actuation to a further embodiment of the device whereby a vane (47) movably displaced by a developing air stream during patient inspiration, completes an electrical circuit containing a battery and a motor driving rotary brushing (43).

Figure 9:
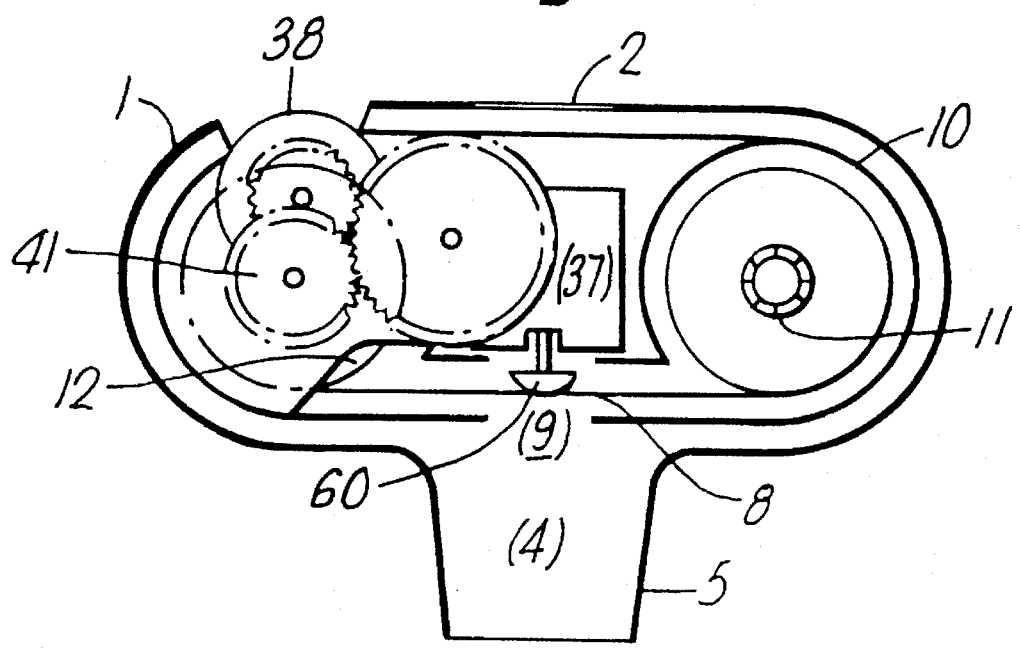
FIG. 9 is a section through an inhaler of the present invention having a cassette comprising spooled carrier storage and take-up means, a recessed wheel driving a gear train for dose advancement and an electromagnetic vibrator.

FIG. 9 illustrates an inhaler of re-usable format with part of the housing and disposable cassette (10) cut away. The cut away illustrates the relative position of carrier storage spool (11) and carrier take-up spool (12) within said cassette to the gear train (41). Sequential advancement of fresh carrier (8) to exposure frame (9) is completed by a recessed dose advance wheel (38) engaging gear train (41) and revolving take-up spool (12). Electromagnetic vibrator (37) is activated by completion of a circuit containing a battery cell. This may be achieved by a push button or the action of a displaceable vane (not shown) as described in FIGS. 8a to 8c. Vibrating head (60) contacting the carrier at the exposure frame causes the release of medicament into chamber (3) where it may be entrained by the patients inspiratory efforts.

Figure 10:
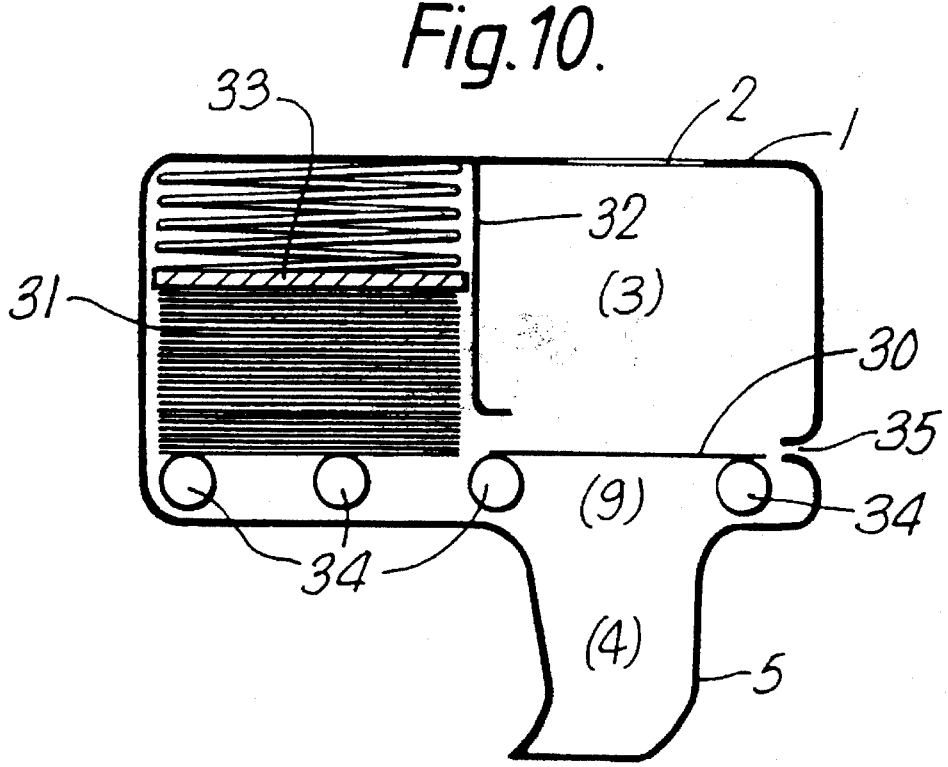
FIG. 10 is a section through an inhaler of the present invention having a carrier comprising a sheaf of sheets.

Referring to FIG. 10, a section through an inhaler of fully disposable format comprising sheets of carrier (30) stored as a sheaf (31) in a storage compartment (32). The sheaf is supported by a spring biased plate (33) such that individual sheets can be advanced by means of rollers (34) which may be sprocketed engaging carrier sheets with suitable apertures in register to an exposure frame (9) prior to aerosolisation. Spent carrier sheets are ejected by rollers (34) through a slot (35) in the housing (1) for disposal by the user.

Figure 11A:
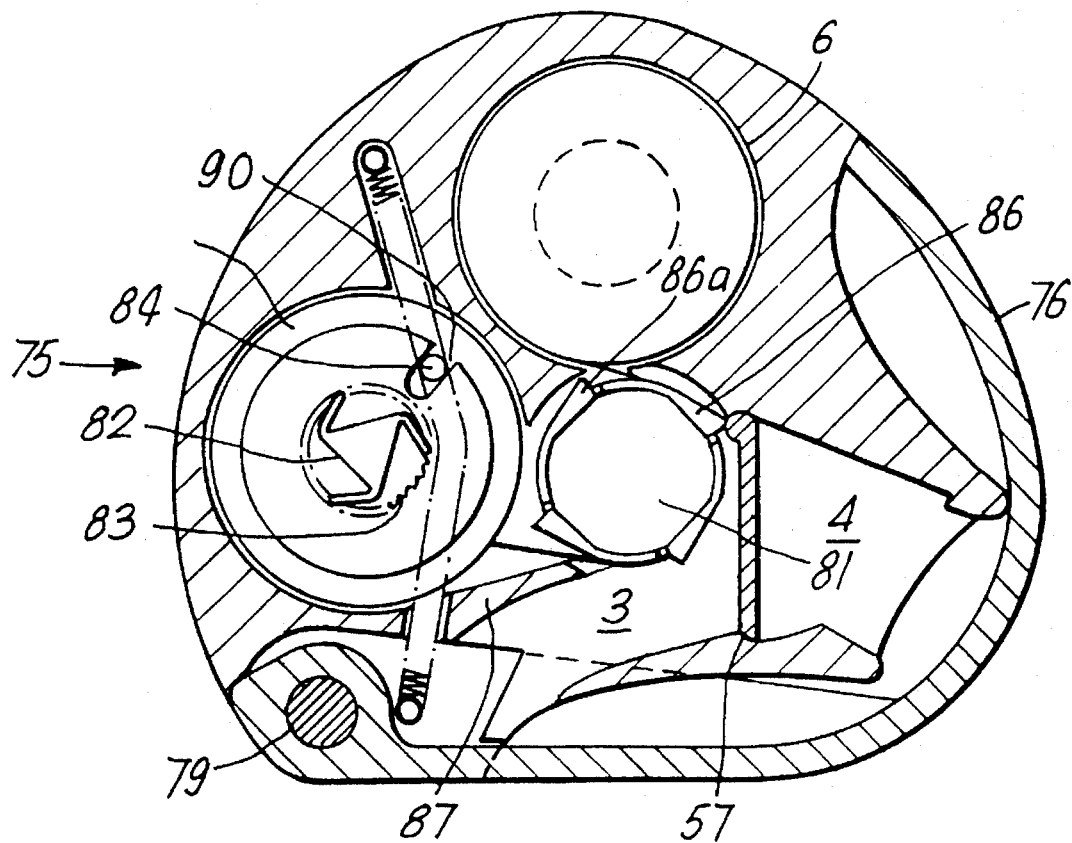
FIGS. 11a to 11c illustrate an inhaler of the present invention, having indirect breath actuation of scraping means for medicament aerosolisation and a housing assembly having a cover.
Figure 11B:
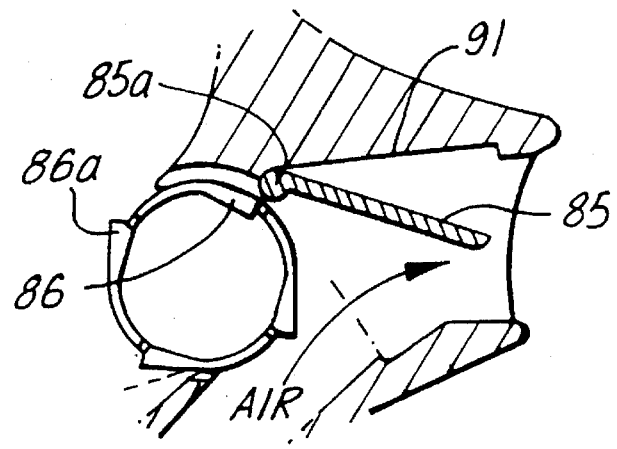
Figure 11C:
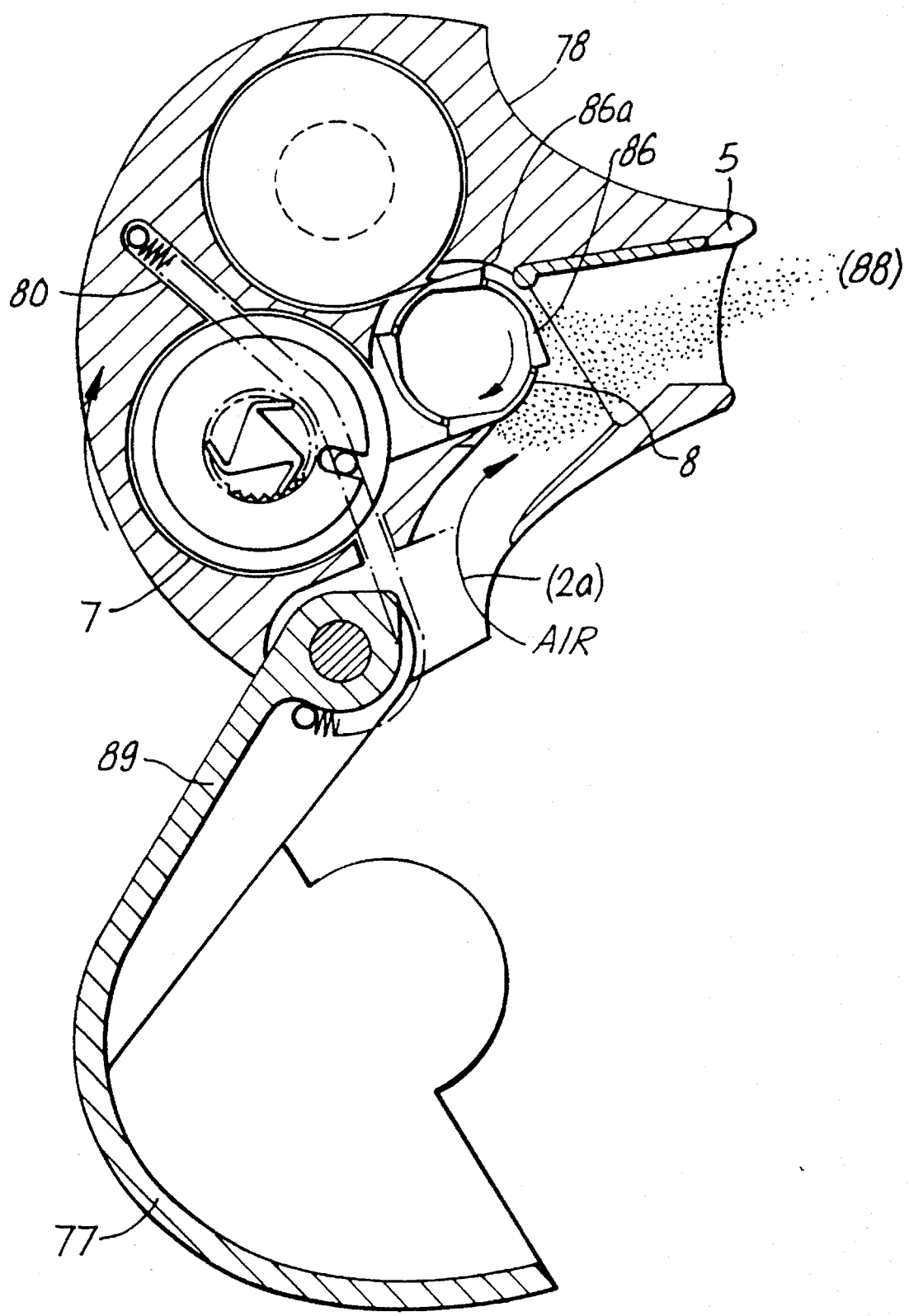

FIGS. 11a to 11c illustrate sections through an inhaler (75) having a housing (76) comprising casing (78) and a cover (77) pivotally mounted at (79) movable between a closed format shown in FIG. 11a and an open format shown in FIG. 11c. The inhaler is maintained in a closed position whilst not in use providing a compact, convenient shape minimising contamination from dirt, moisture ingress etc.

The housing has one or more integral air vents (2*a*), which are exposed when the device is in the open format, and defines an aerosolisation chamber (3) in communication with a patient port (4), having a mouthpiece adaptor (5). Within the chamber are integral carrier storage spool (6), idler (81) having four lobed catches (86) of equal dimension, and carrier take-up spool (7) having a pawl (82) and ratchet (83) allowing unidirectional rotation of the spool (indicated by the arrow of FIG. 11*c*).

The device is cocked for use by fully opening the cover (77) causing tensioning of the device spring (89) which acts on drive peg (84) which is engaged in a slot (90) in carrier take-up spool (7). Rotation of take-up spool (7) by the drive peg (84) is prevented by the engagement of displaceable idler catch (86) with vane pivot axle (85*a*). Opening the device exposes the patient port and mouthpiece adaptor to the patient.

FIG. 11*b* illustrates the actuation of the device by a developing airstream as the patient inhales. Vane (85) provides indirect breath actuation means and may additionally prevent through device exhalation by the patient. The vane is pivoted so as to be displaceable when an airflow is generated through the device from the exterior via vents (2*a*) to the patient port (4). Unidirectional displacement of vane (85) is provided by the vane engaging stop (57). The vane may have a width equal to the patient port such that upon exhalation the vane sealingly contacts stop (57) preventing the ingress of moist, exhaled air. In the home (non-displaced) position the vane engages catch (86) preventing carrier uptake. Inhalation displaces vane (85) into recess (91) whilst displacing and freeing idler catch (86) from engagement by vane pivot axle (85*a*) and allowing idler (81) to complete the cycle until the following catch (86*a*) re-engages the vane pivot axle. The curvature of each catch aids the stepwise engagement of vane pivot axle (85*a*) to define dosage lengths of carrier.

Referring to FIG. 11*c*, medicament is removed from the carrier by a combination of the patient's inspiratory effort, acceleration/deceleration impaction and the action of scraper (87). With idler (81) free from interruption the tensioned spool (7) rapidly winds up carrier (8) under the influence of drive spring (89) moving drive peg (84) until the passage of idler (81) is abruptly halted by the next catch (86*a*) re-engaging pivot axle (85*a*). The resulting momentum of medicament particles, the impaction due to the arresting of carrier velocity and the resulting vibration of the carrier aid medicament removal. The curvature of idler (81) bends the carrier with drug coating outwards as each new unexposed section is indexed onto the idler (81) and exposed to the airstream, thereby easing the release of powder. Scraper (87) aids the release of medicament by contacting the exposed area of carrier prior to take-up and mechanically displaces the medicament particles. After use the device is returned to the closed-format by the patient, the drive peg (84) being returned to its original position under the influence of return spring (80).

FIGS. 12*a* and 12*b* illustrate alternative embodiments of a variation of the inhaler illustrated in FIGS. 11*a* to 11*c*. Both devices are shown in the inactive closed format.

FIG. 12*a* illustrates an inhaler (93) having a spring biased cam follower comprising a spring (95), biasing wheel mounting (96) and bearing cam follower wheel (97). Cam follower wheel (97) engages and travels the surface of cam (98) during cam rotation. Cam (98) has an essentially square cross section and abuts idler (99) having four displaceable catches (100) of equal dimensions. Vane (85) provides indirect breath actuation means and may form a one way valve preventing exhalation through the inhaler. The device is cocked as described previously for FIGS. 11*a* to 11*c*, movement of the carrier being prevented by engagement of catch (100) with vane pivot axle (85*a*).

When the patient inhales, vane (85) is displaced into recess (91). Idler (99) is no longer blocked allowing carrier (8) to be drawn onto take-up spool (7). As the carrier is taken up, passage of cam follower wheel on the surface of cam (98) for the first 45° of rotation compresses spring (95) such that during the second part of the cycle (a further 45° rotation), cam follower wheel (97) causes the cam to rotate faster than take-up spool (7). A loop of carrier (not shown) develops until idler (99) rotation is prevented by engagement of following catch (100*a*) with vane pivot axle (85*a*). Subsequently the loop of carrier is snapped tight by take-up spool (7) causing release of medicament into the airstream.

FIG. 12*b* illustrates an inhaler (105) having a cam assembly comprising a central cam (107) of essentially square cross section abutting a guide wheel (108) bearing carrier (8) and an interrupter wheel (109) having, at the four compass positions, circular elements (110) of equal dimensions and freely rotatable about axis; a spring biased cam follower comprising a spring (95) biasing wheel mounting (96), supporting cam follower wheel (97) and an interrupter assembly comprising a rocker arm (112) pivoting about pivot point (112a) and bearing a peg (114) and a catch (115) having a spring leaf (116). Catch (115) is able to pivot about pivot point (113). Cam follower wheel (97) engages and travels the surface of central cam (107) during rotation of the cam assembly. Rocker arm (112) is biased by the action of a weak spring (117), fixed between peg (118) of housing (1) and slot (119), such that the rocker arm nose (112b) stepwise engages circular elements (110) at every 90° rotation of the cam assembly.

The device depicted illustrates alternative embodiments to the format of the drive (89) and return (80) springs described previously and the idler/ratchet mechanism ensuring unidirectional rotation of carrier take-up spool (7).

Figure 12A:
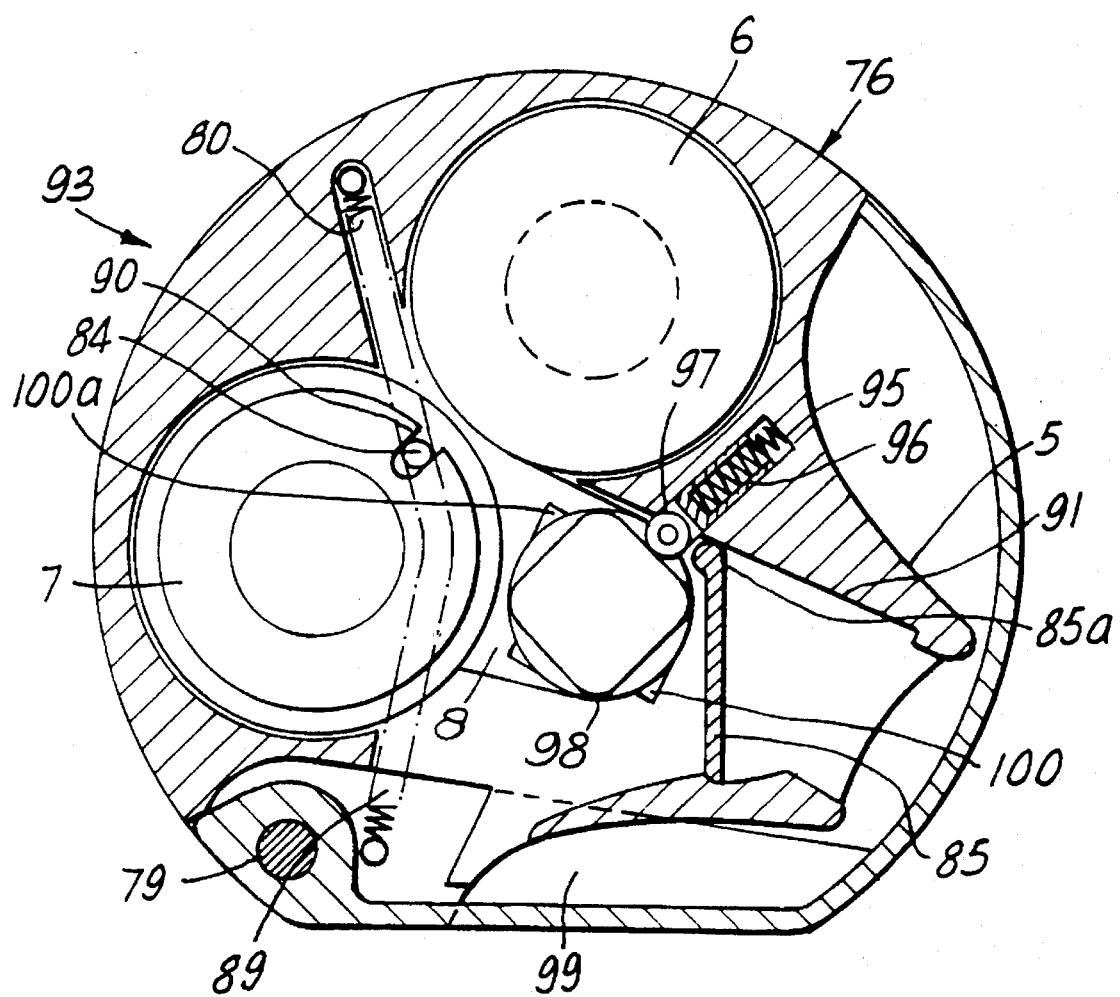
FIGS. 12a and 12b illustrate sections through alternative inhalers of the present invention.
Figure 12B:
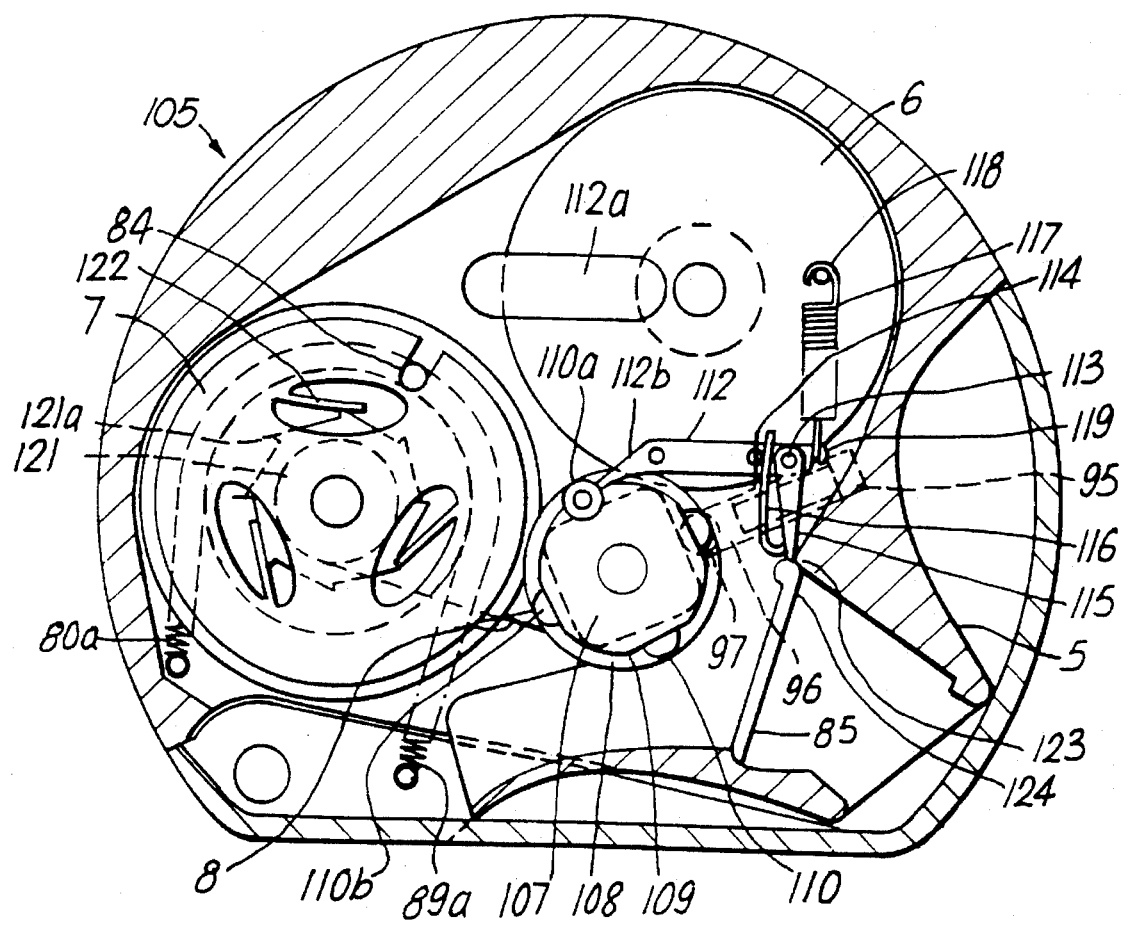

In use, the device is cocked as described for FIGS. 11a, 11c and 12a by opening of the cover, whereby drive peg (84) is tensioned by the activity of drive spring (89a). Unidirectional (clockwise) rotation of take-up spool (7) is effected by the action of spindle (121) having a series of stepped projections (121a) engaging the spring leaves (122) of the spool in the reverse (anti-clockwise) direction. Tensioned drive peg (84) imparts a slight rotation to take-up spool (7) causing tightening of any slack carrier (8). Rotation of the take-up spool (7) is prevented by the engagement of rocker arm (112) to the interrupter wheel (109), but the rocker nose (112b) is caused to be displaced slightly on the circular element (110a). The slight lift imparted to the rocker nose (112b) in a reciprocal motion about the pivot causes catch (115) to engage the curved surface (123). The curved surface (123) directs catch (115) to rest upon vane (85). Vane (85) provides indirect breath actuation.

Patient inhalation through mouthpiece adaptor (5) displaces vane (85) into recess (91) as described previously. Rotation of the vane about pivot point (124) causes the displacement of catch (115). As catch (115) is displaced from a blocking to a non-blocking position, rocker arm (112) is lifted by interrupter element (110a) thus allowing rotation of cam assembly. Rocker arm (112) is maintained in contact with surface of interrupter wheel (109) by spring (117) so that it contacts the following interrupter element (110b). This provides a stepwise mechanism (every 90° rotation of the cam assembly) for carrier exposure. Co-operation of central cam (107) and spring biased cam follower cause a loop of carrier to be formed which is snapped tight causing release of medicament particles as described in FIG. 12a.

Figure 13:
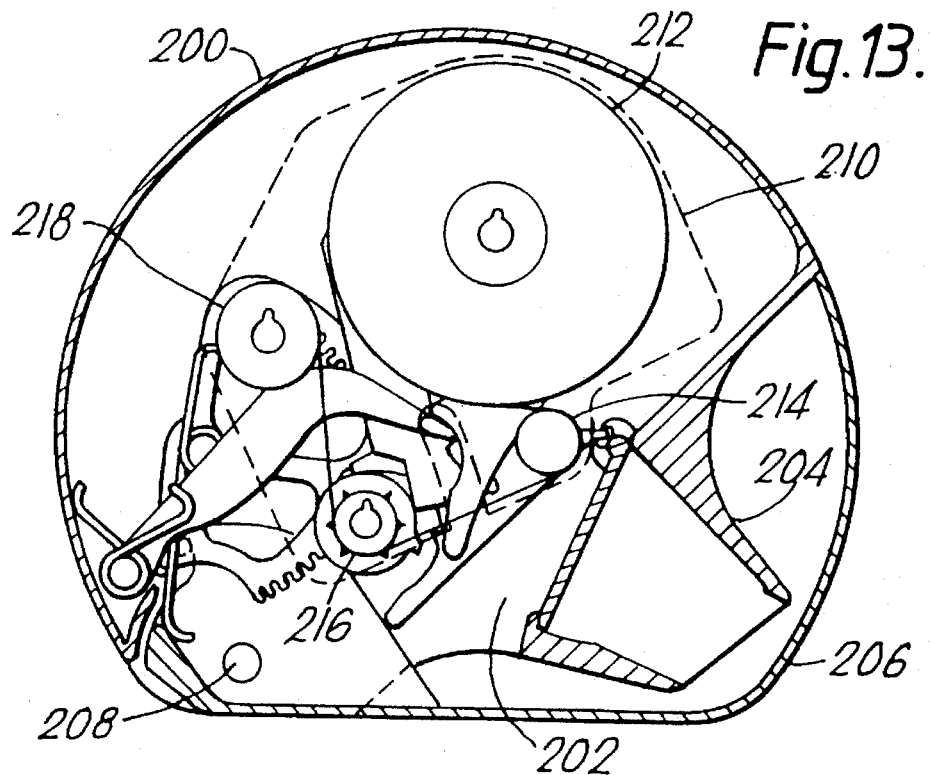
Figure 14:
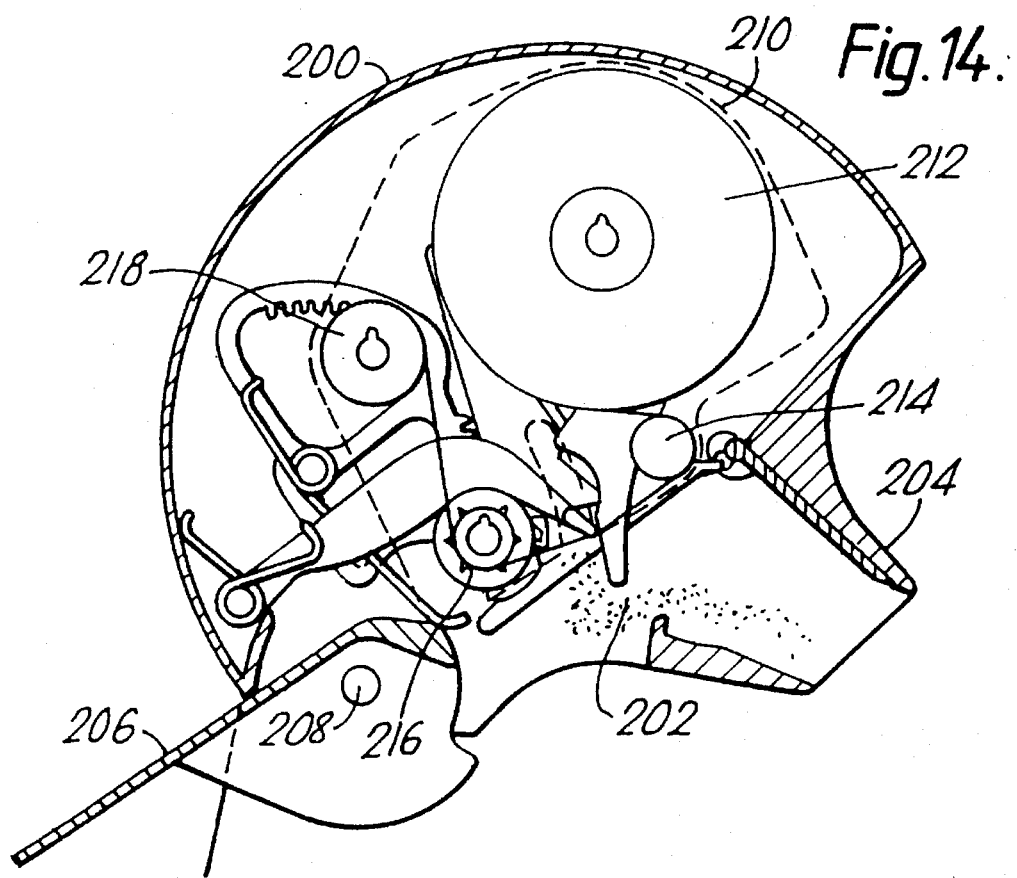

FIGS. 13 and 14 represent a cross-section through a further inhalation device in accordance with the invention showing the device with the cover closed for storage and with the cover open in the dispensing position respectively.

The device comprises a housing (200) defining a chamber (202) in communication with a mouthpiece (204). A cover (206) is pivotable about pivot point (208) between a closed position as showed in FIG. 13 in which the contents of the device are protected against ingress of moisture and contaminates, and a dispensing position, ready for patient's use, as shown in FIG. 14.

The housing (200) contains an elongate carrier bearing powdered medicament which is held within a removable cassette shown in dotted outline at (210). The cassette comprises a supply spool (212) which initially holds the bulk of the elongate carrier wound in the form of a roll. From the supply spool the elongate carrier passes round an idler roller (214) and a spiked control roller (216) to a take-up spool (218). An area of the elongate carrier between the idler roller (214) and the spiked control roller (216) is exposed to the chamber (202); when the device is actuated powdered medicament from this exposed area is released from the elongate carrier and entrained in the patient's airflow through the chamber.

The device is very simple to operate requiring only that the patient opens the cover (202) and inhales through the mouthpiece (204). This action activates a fairly complex sequence of operation of four separate mechanisms. These mechanisms comprise a driving mechanism for advancing the elongate carrier, driven by a spring which is cocked by opening the cover; a trigger mechanism which ensures the energy stored in cocked drive spring is not released until inhalation is sensed, an impaction mechanism which causes the exposed area of the elongate carrier to be impacted ensuring release of medicament into the air stream and a braking mechanism which holds the elongate carrier taut while the impaction takes place. For ease of comprehension the components and action of the individual mechanisms will be described separately.

Figure 16:
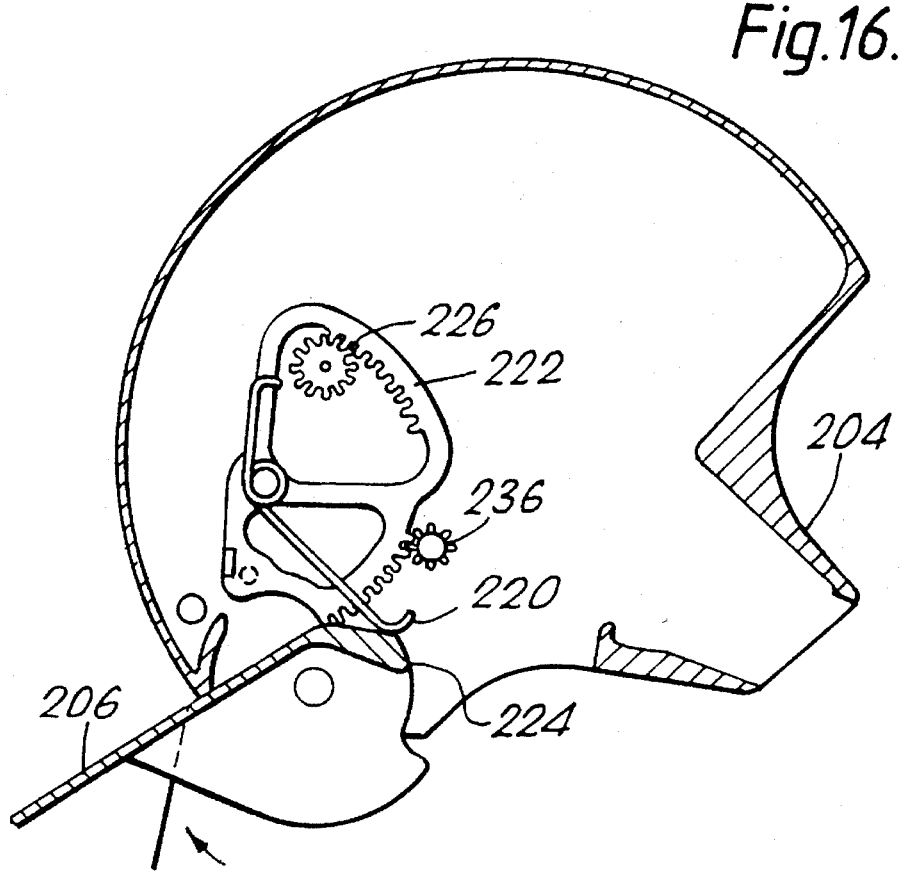
Figure 17:
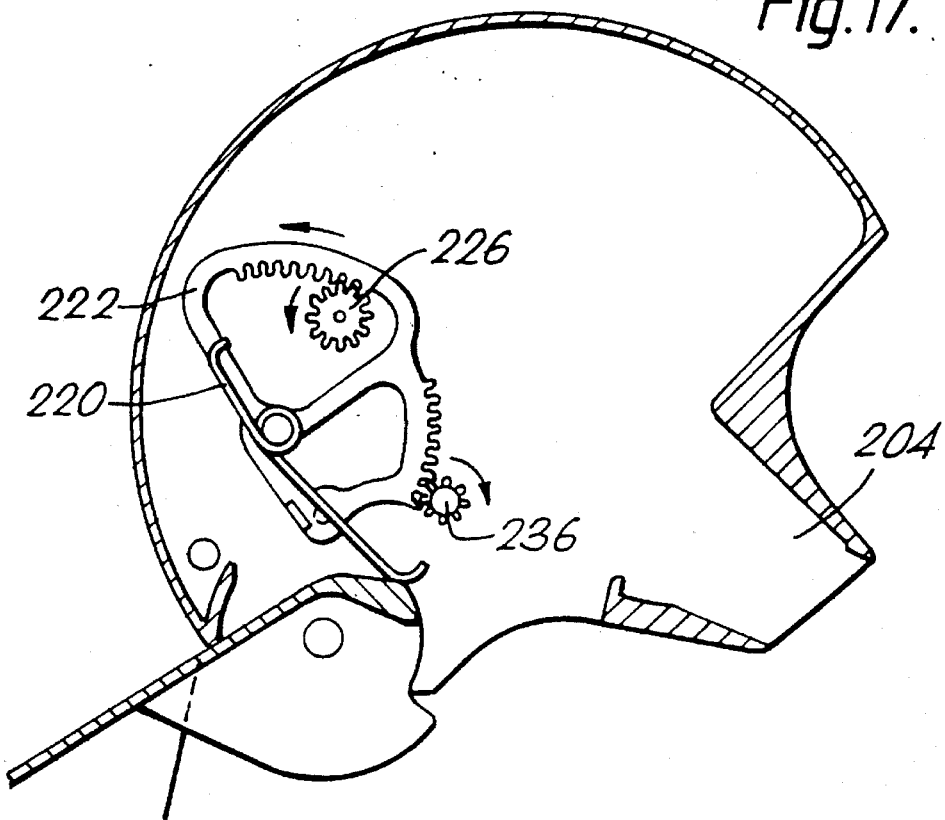

FIGS. 15 to 17 illustrate the drive mechanism for advancement of the elongate carrier. The drive mechanism comprises a drive spring (220) positioned between the drive gear (222) and the portion (224) of the cover (206); when the cover (206) is closed over the mouthpiece it is lightly held shut by the action of the drive spring.

FIGS. 15a, 15b and 15c, represent cross-sections at different heights through the drive arrangement generally shown within the circle (I) for the take-up spool (218) of the cassette (210) (shown in FIGS. 13 and 14). The drive from the take-up spool pinion (226) is transmitted via a spring (228) and ratchet arrangement comprising a ratchet gear (230) and ratchet pawl (232) to a spool-driving peg (234) which engages with the take-up spool of the cassette. The spring (228) allows the drive gear to move the pinion through a greater angle of rotation than the elongate carrier allows the spool to move. The ratchet arrangement allows the drive gear to be reset without unwinding the tape from the take-up spool.

FIGS. 15d and 15e represent cross-sections at different heights within the circle (II) and illustrate how the drive from the control roller pinion (236) is transmitted via a ratchet mechanism comprising a ratchet gear (238) and a pawl (240) mounted on the control roller pinion so that the mechanism may be reset without moving the control roller and elongate carrier. The casing of the ratchet gear (238) is in the form of an escape wheel having stops (242) which interact with the triggering mechanism to limit the movement to one revolution per cycle. The drive from the control roller pinion is finally transmitted to the control roller via a drive spigot (244).

FIG. 16 shows the cover (206) opened to expose the mouthpiece and to cock the drive or advancement mechanism by applying pressure to the drive spring (220) caused by movement of the portion (224) of the cover when the cover is pivoted about its pivot point. Although the drive spring (220) is loaded the drive gear and associated pinions cannot move as the control idler is locked by the escapement (242) (FIGS. 15d and 15e).

When the escapement releases the control idler, movement of the drive gear (222) and associated pinions (226 and 236) is effected under the influence of the drive spring (220), the direction of movement of the components being shown by the arrows on FIG. 17.

Figure 18:
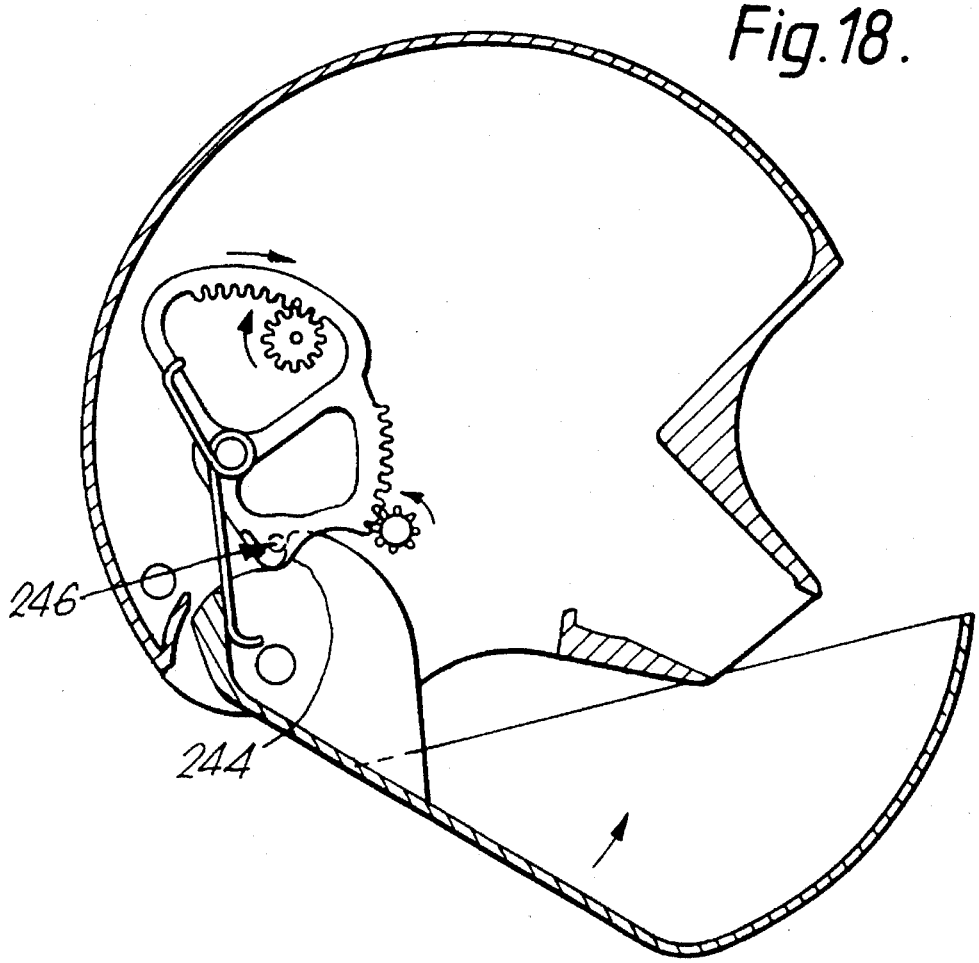
Figure 19:
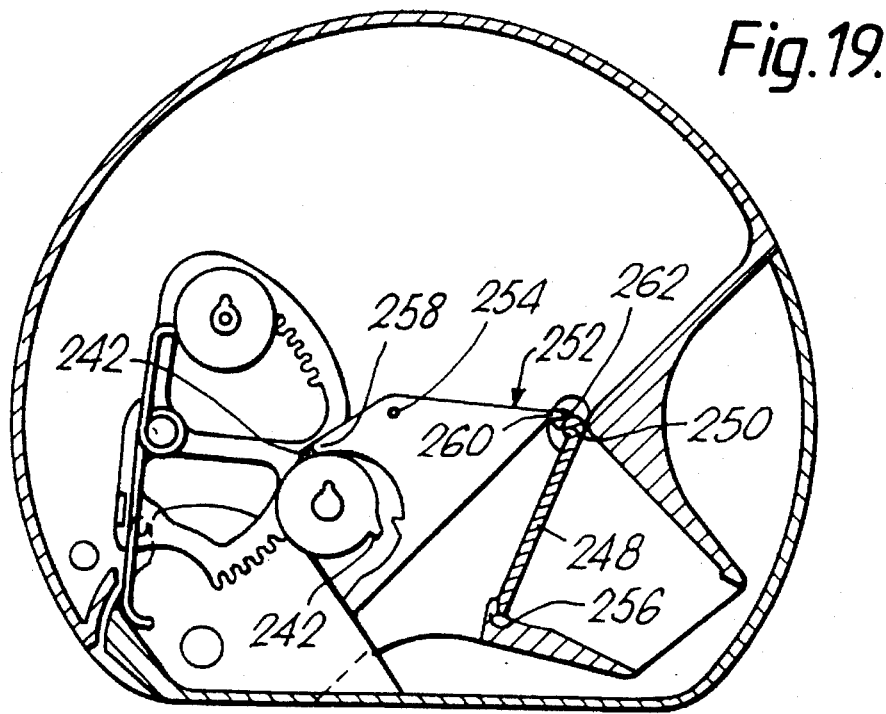

After actuation of the device, when the cover is closed as shown in FIG. 18, a step (244) on the cover (206) engages a spigot (246) on the drive gear (222) returning the drive mechanism to its initial position and causing rotation of the pinions (226 and 236) as shown by the arrows in FIG. 18.

The components and mode of action of the breath actuated triggering mechanism is depicted in FIGS. 19 to 23.

Figure 20:
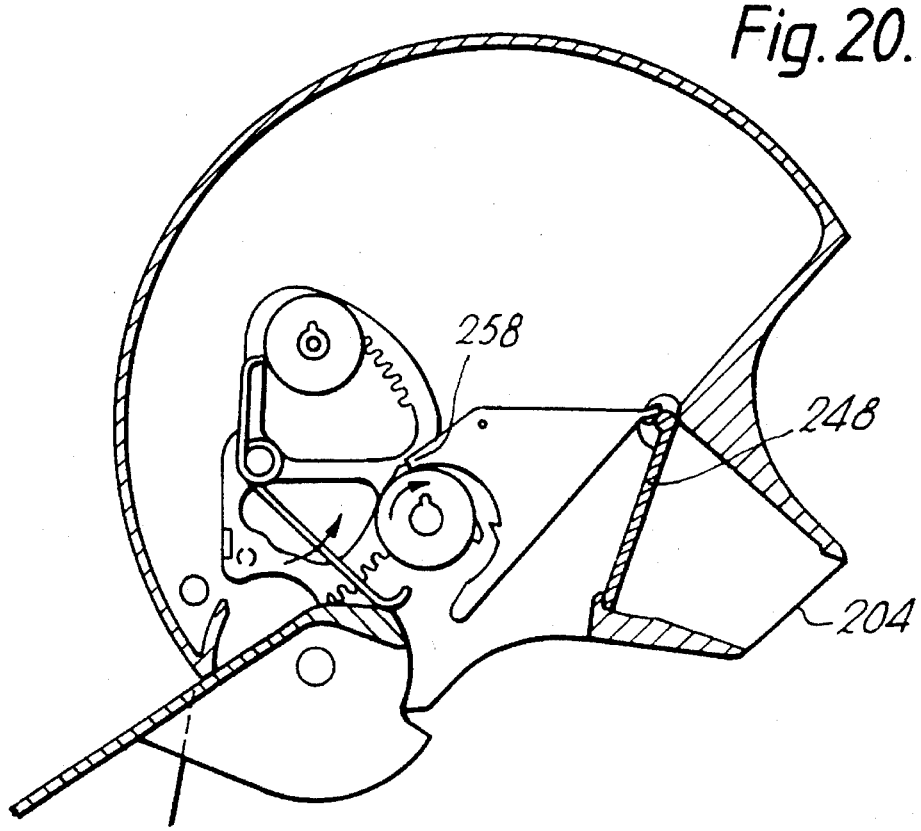
Figure 21:
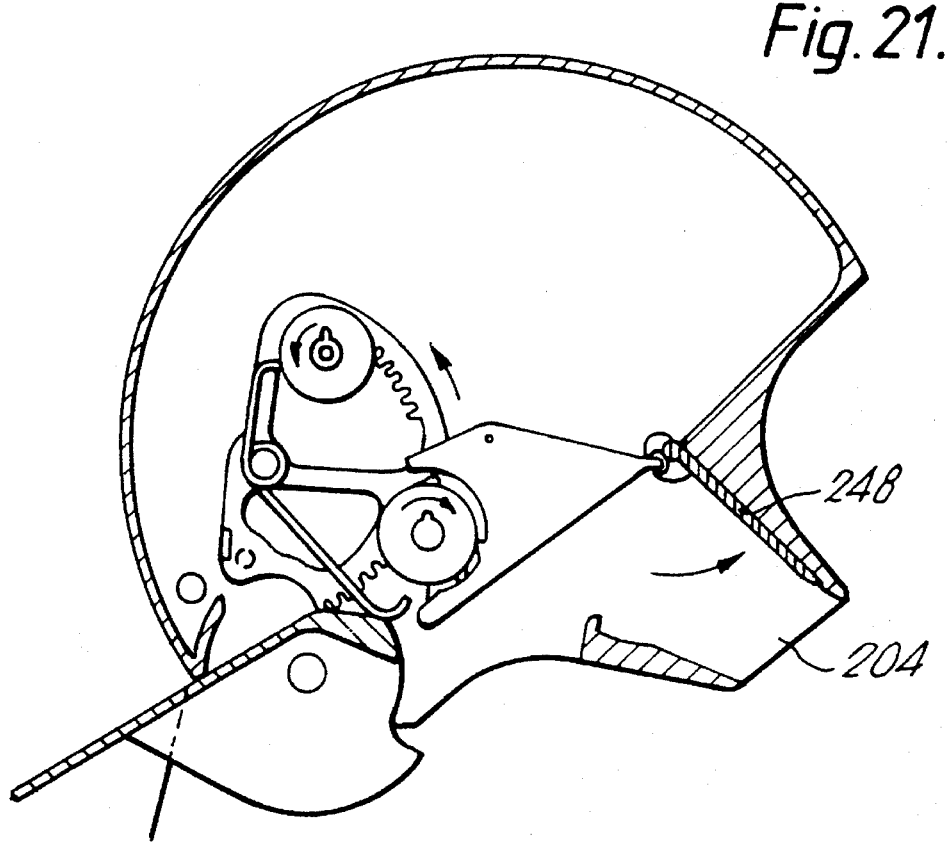
Figure 22:
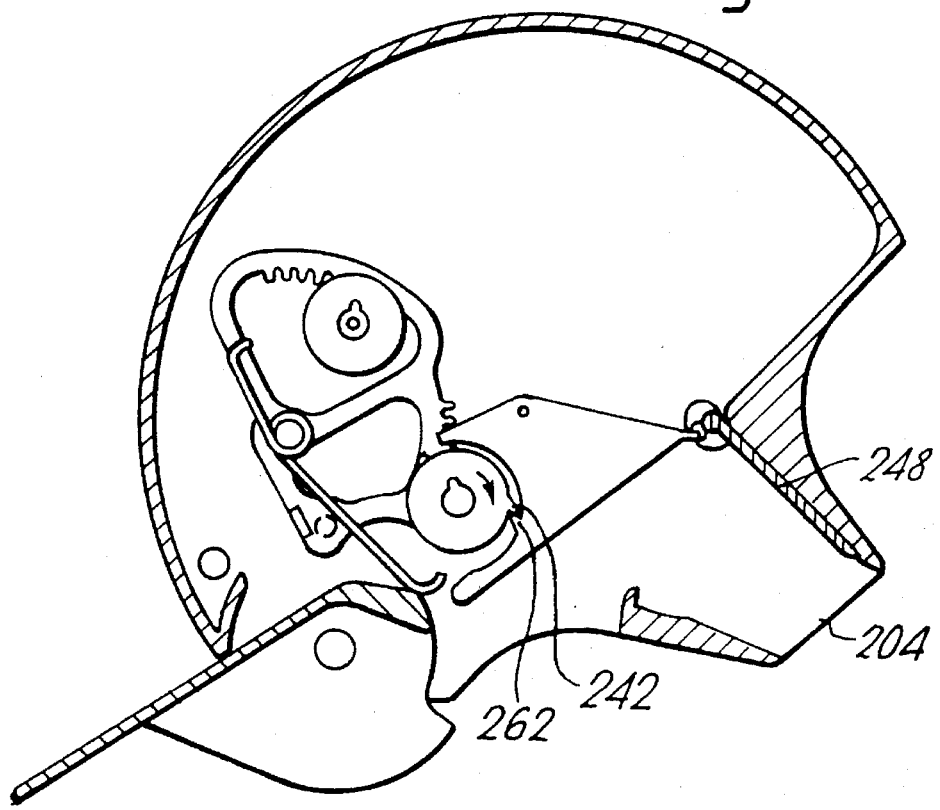

In addition to the escape wheel comprising stops (242) on the control idler shaft, the triggering mechanism comprises a pivoting vane (248) which is capable of pivotal movement about pivot point (250), and an escapement lever (252) which is pivoted about pivot point (254). When the vane is closed and abuts stop (256) the step (258) on the escapement lever abuts stop (242) on the escape wheel. Pivotable movement of the escapement lever (252) is prevented by engagement of a projection (260) on the escapement lever with a curved abutment surface (262) formed near the pivot point (250) of the vane. When the cover is opened as shown in FIG. 20, the drive spring (220) is tensioned but movement of the drive gear (222) and the control roller (236) in the direction of the arrows is prevented by the escapement wheel. When the patient breathes through the mouthpiece the vane (248) is lifted by the airflow as shown in FIG. 21. Movement of the vane (248) allows pivotal movement of the escapement lever (252) moving the step (258) on the escapement lever away from the stop (242) on the escapement wheel thereby allowing rotation of the control roller pinion (236), the gear train (222) and the take-up spool pinion (226). Rotation of the pinions (226 and 236) causes rotation of their associated spigots (234 and 244) thereby rotating the take-up spool (218) and control roller (216) of the cassette (210).

When the control roller (216) has completed almost one revolution, a second stop (242) on the secape wheel contacts step (262) of the escapement lever (252) (FIG. 22) and the control roller and hence the elongate carrier are arrested.

Figure 23:
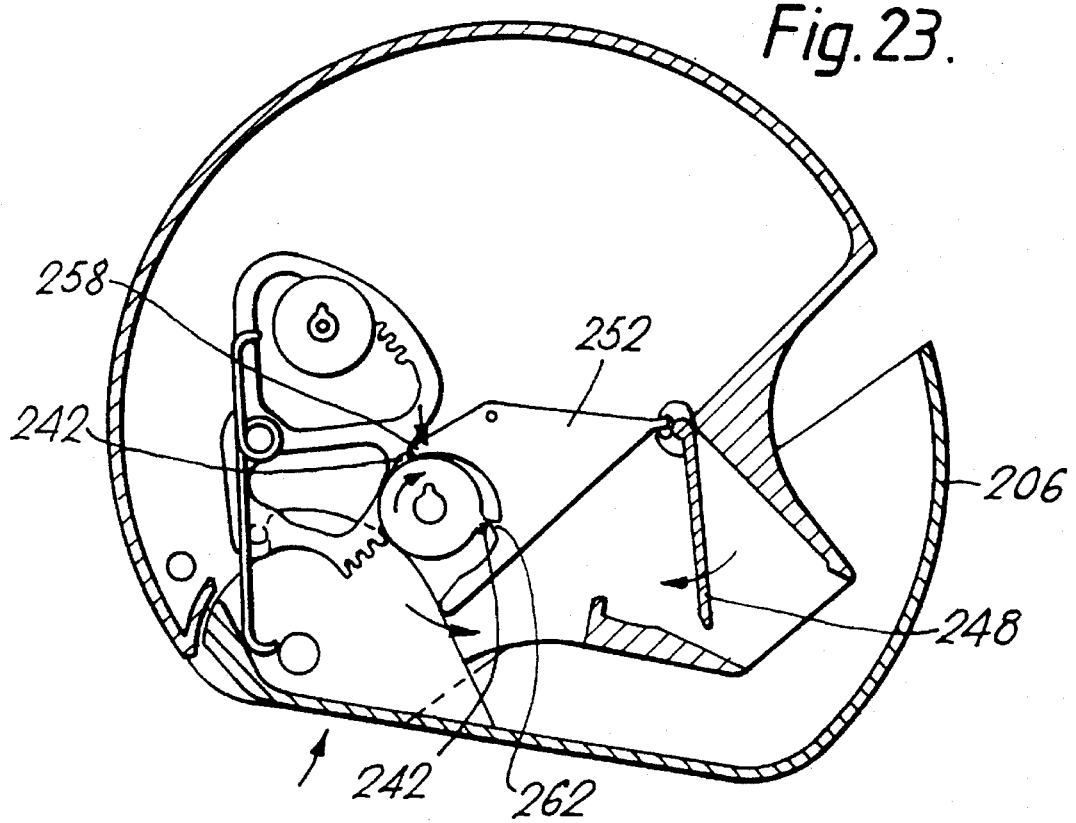

After the device has been used and the cover (206) is closed the vane pivots back to its closed position and the escapement lever (252) is pushed up to release the engagement between the step (262) and the escapement wheel and step (258) on the escapement lever (252) engages the stop (242). The movement of the various components is depicted in FIG. 23 by the arrows.

Figure 24:
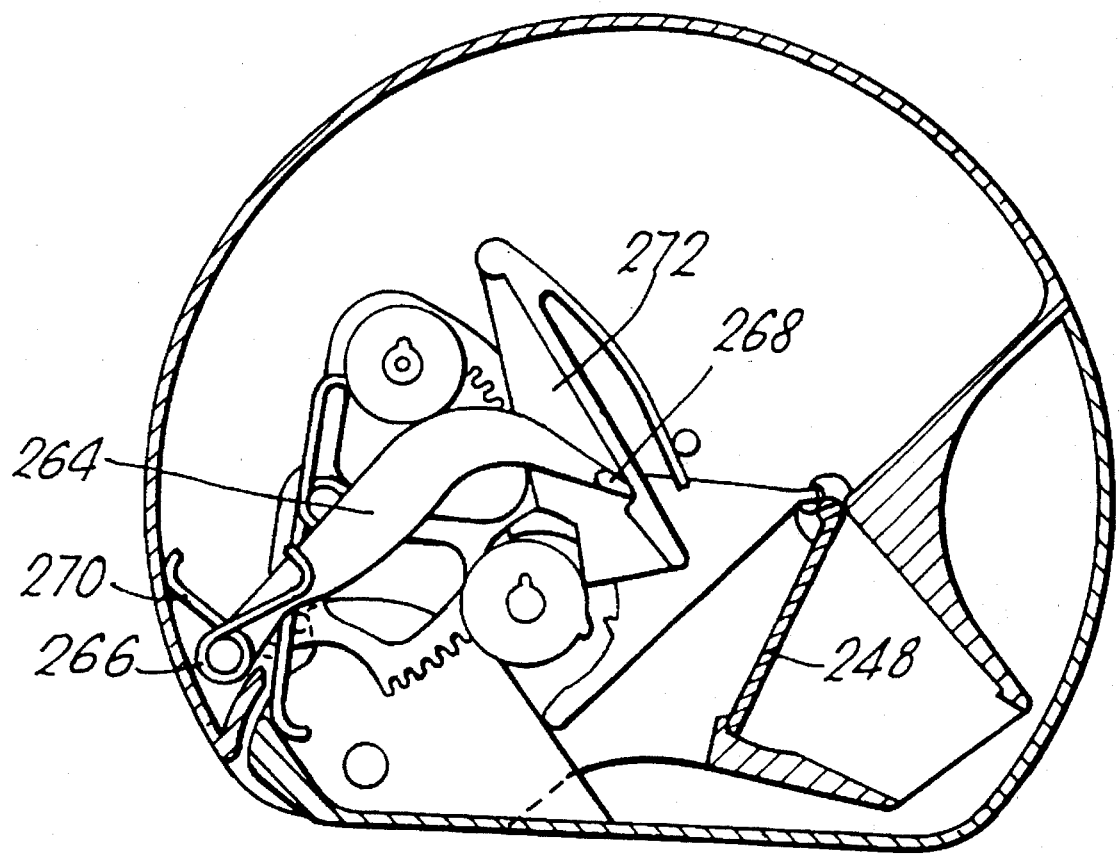
Figure 25:
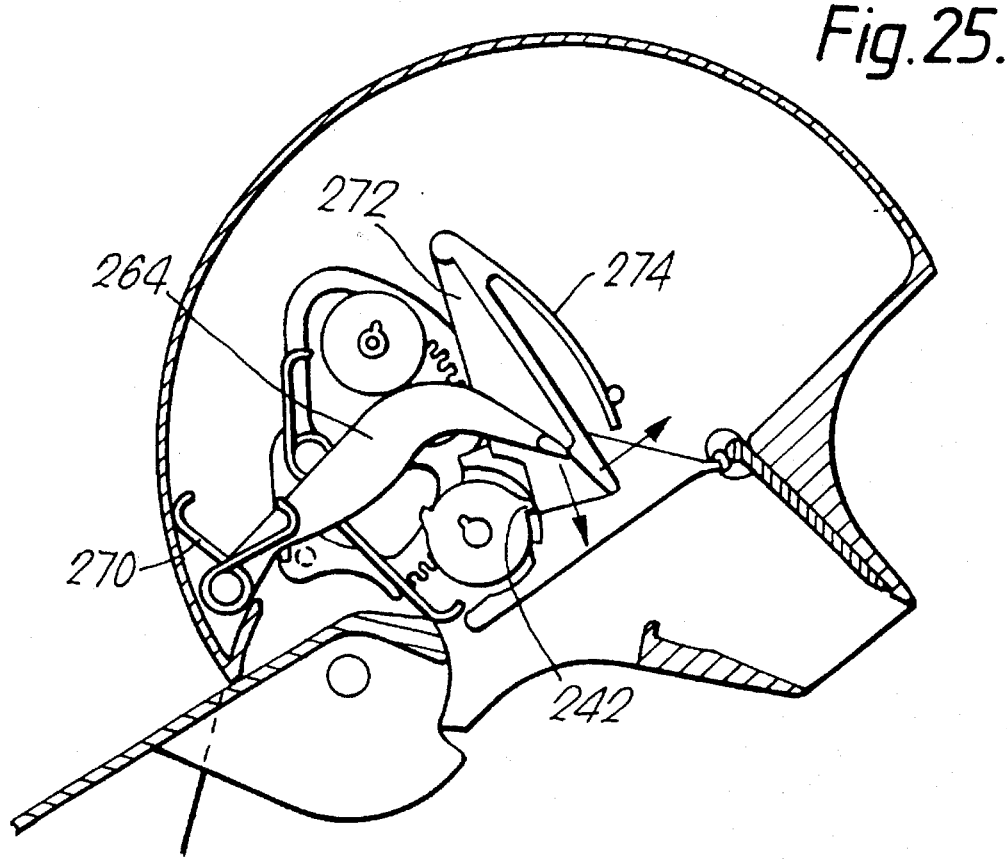
Figure 26:
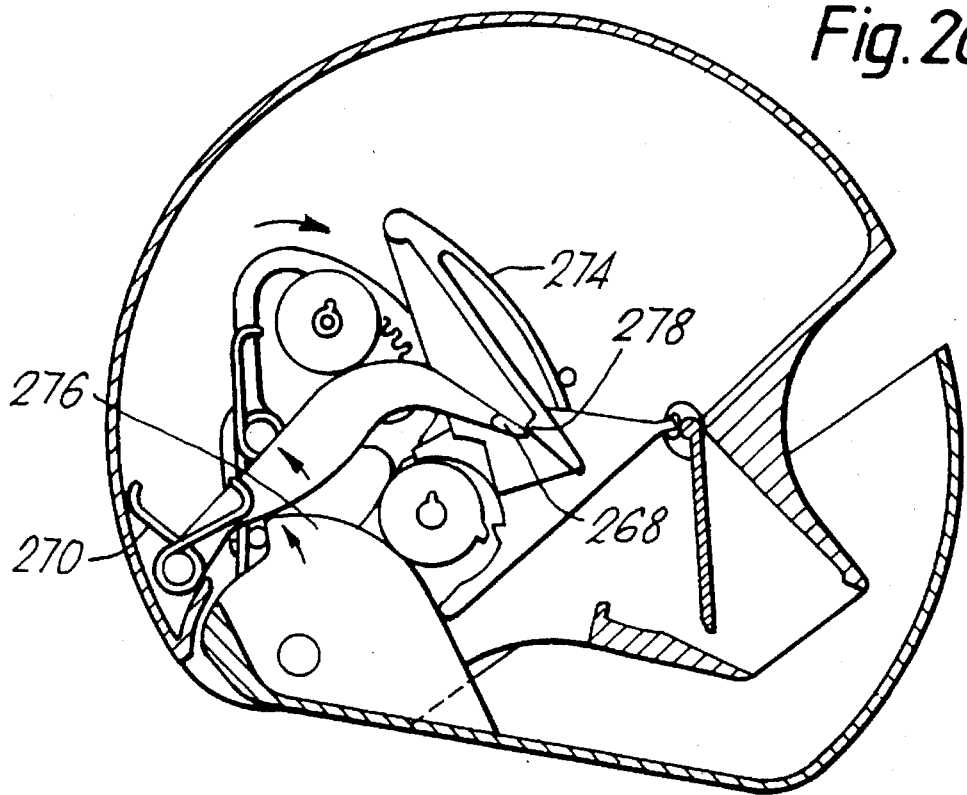
Figure 27:
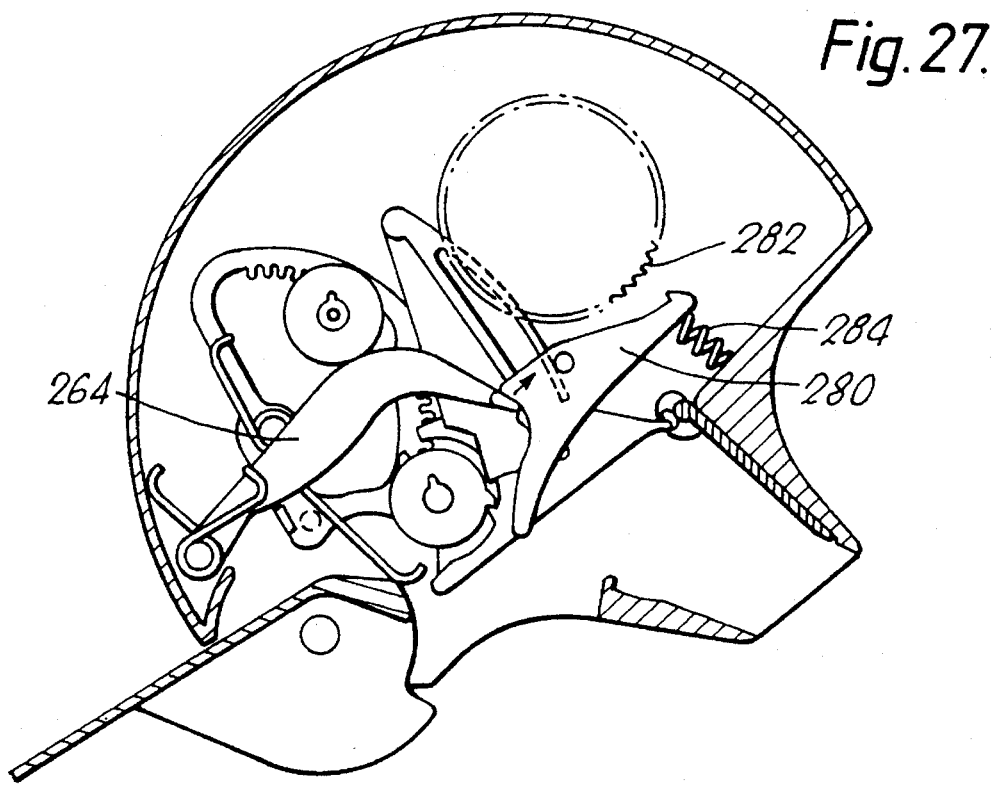
Figure 28:
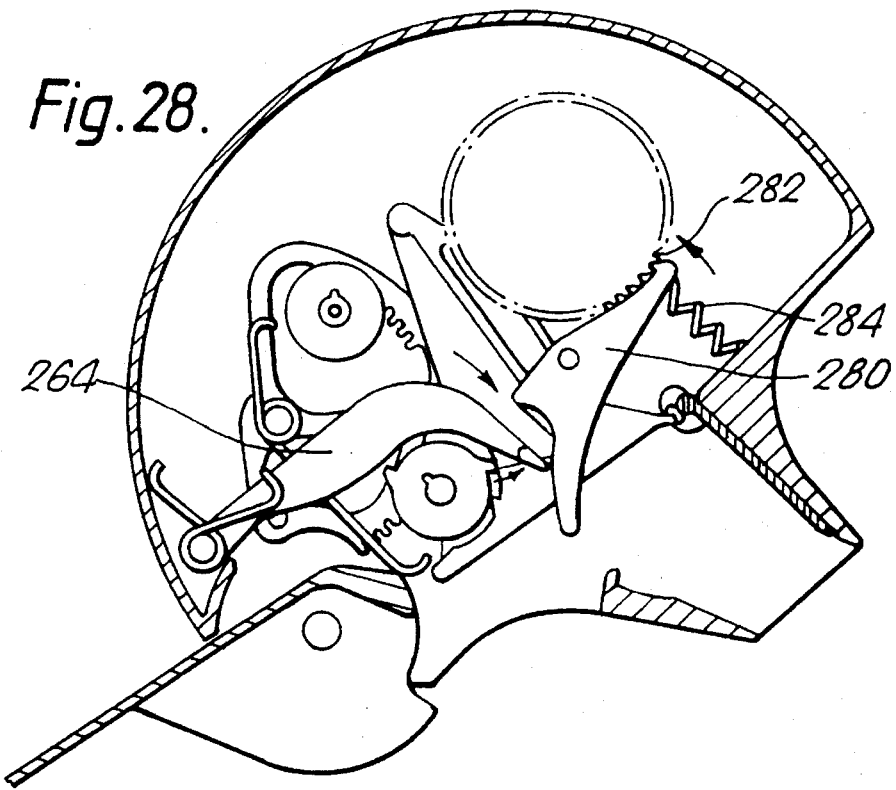
Figure 29:
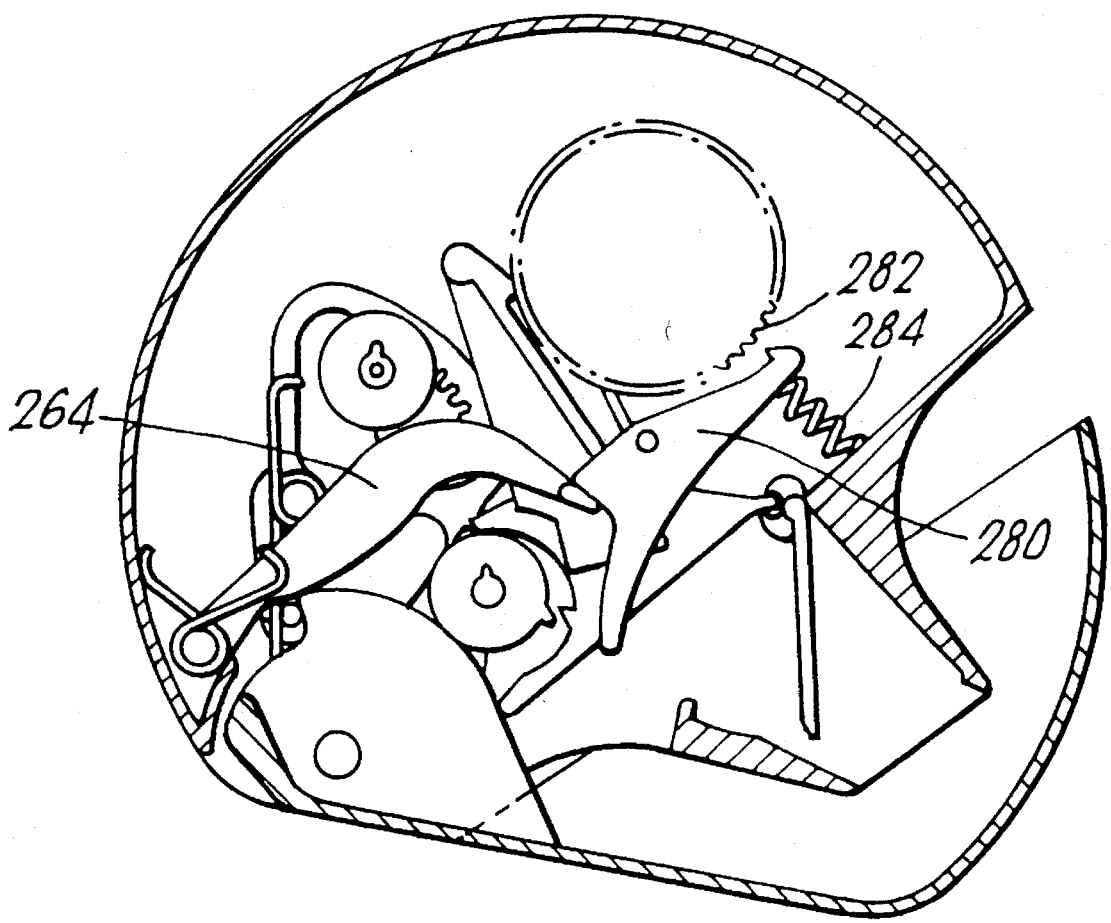
Figure 30:
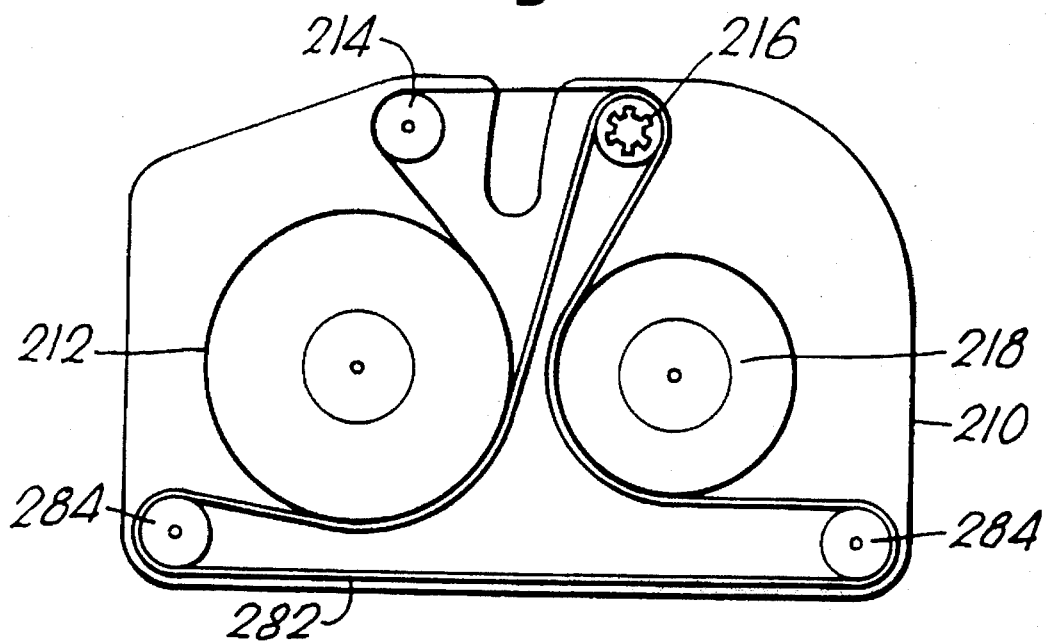
FIGS. 30 and 31 represent cassettes containing elongate carrier in accordance with the invention, and, FIGS. 32 to 35 represent cross-sections through devices in accordance with the invention adapted to contain the cassettes of FIG. 30 or FIG. 31.
Figure 31:
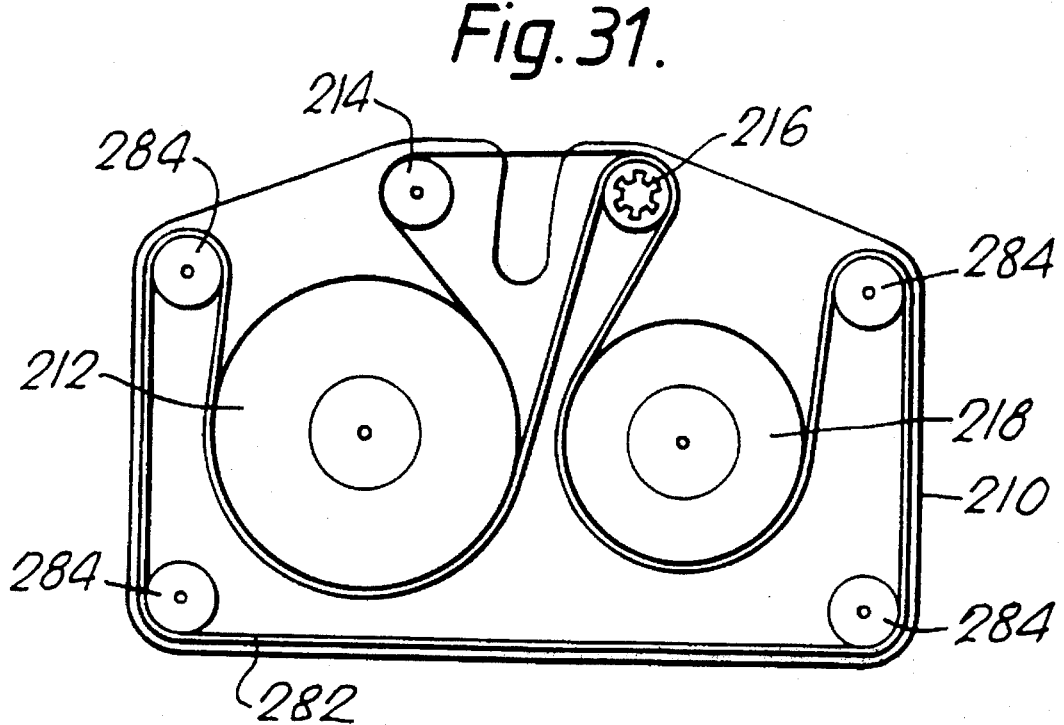

The device comprises means to facilitate release of the powdered medicament from the elongate carrier in the form of an impaction mechanism which is depicted in FIGS. 24 to 26. After the patient has begun to breathe through the mouthpiece releasing the triggering mechanism, and the elongate carrier has been advanced by the drive mechanism, the area of the carrier exposed to the chamber is struck by an impactor arm driven by a powerful spring to release medicament from the elongate carrier into the air stream.

FIG. 24 shows the impactor mechanism comprising an impactor arm (264) which is pivotally mounted about pivot point (266) and has an impaction head (268) which strikes the elongate carrier (not shown). The impactor arm is biased by spring (270). The impactor arm is held clear of the elongate carrier by a catch (272) which engages the impaction head (268) until the triggering mechanism is activated. When the triggering mechanism has activated the drive mechanism and the escapement wheel rotates, one of the stops (242) acts as a cam to push the catch (272) against its integral spring (274) and releases the impaction head thereby allowing pivotal movement of the impaction arm under the influence of the spring (270) so that the impaction head strikes the exposed area of the elongate carrier (not shown). The direction of movement of the catch (272) and the impaction head (268) is shown by the arrows in FIG. 25.

FIG. 26 shows the impaction device being reset during closing of the cover (206). Cam surface (276) is provided on the cover which bears against the impactor arm turning it to its original position and compressing spring (270). During this movement the impaction head slides up catch (272) initially moving the catch back against its integral spring (274) until the impaction head is clear of the stop (278) of the catch and thereafter the catch moves to its blocking position engaging the impaction head under the influence of its integral spring (274).

In order to ensure efficient release of powdered medicament from the elongate carrier it is necessary that the exposed area of the elongate carrier is held taut while being struck by the impactor head. The control roller and take-up spool prevent the elogate carrier from retreating by virtue of the ratchet arrangements described with reference to FIGS. 15*b* and 15*d*. In order to prevent the carrier spool from unwinding during impaction, the carrier spool is arrested just prior to impaction by means of a pawl which engages a ratchet wheel (282) attached to the carrier spool shaft. Normally, the pawl (280) is held out of engagement with the ratchet (282) by contact with the impaction head (268) of the impactor arm (264) (FIG. 27), but once the impactor arm moves towards the elongate carrier, the pawl (280) springs into engagement with the ratchet (282) under the influence of spring (284) (FIG. 28). This engagement prevents further rotation of the carrier spool thereby arresting the advancement of the elongate carrier, securely holding the length of the elongate carrier between the carrier spool and control roller so that the impaction head strikes the taut elongate carrier thereby imparting sufficient energy thereto to cause powdered medicament to be released into the air flow caused by the patient's inspiration through the mouthpiece.

During closing of the cover (206) movement of the impactor arm resets the pawl (280) lifting it out of engagement with the ratchet (282) and compressing spring (284) (FIG. 29).

FIGS. 30 and 31 represent alternative forms of cassettes containing an elongate carrier bearing powdered medicament in accordance with the invention. Each cassette (210)comprising supply spool (212), an idler roll (214), a control roller (216) and a take-up spool (218). The elongate carrier passes from the supply spool around the idler and control rollers to the take-up spool.

The cassettes of FIGS. 30 and 31 differ from that shown in FIGS. 13 and 14 in that they possess an integral drive belt (282). The purpose of the belt is to keep the rotational movement of the supply and take-up spools in precisely the correct relationship to each other and to the control roller regardless of the proportion of elongate carrier that has been passed from one spool to another. This objective is achieved by the drive belt (282) being in frictional contact with the control roller (216) (beneath the elongate carrier), and with the outside surface of the elongate carrier on each of the spools. In order to achieve the necessary arc of contact between the drive belt (282) and the elongate carrier on the spools, the cassette additionally comprises rollers (284). The elongate carrier is advanced simply by driving the control roller (216) which causes the correct rotational movement of each spool. As each spool is driven directly by the control roller (216), additional mechanisms to arrest the carrier spool and to wind the elongate carrier on to the take-up spool are no longer required.

FIGS. 32 to 35 illustrate an inhalation device in accordance with the invention suitable for use with the cassettes of FIGS. 30 and 31. The cassette of FIG. 30 is shown in the device of FIGS. 34 and 35.

Figure 32:
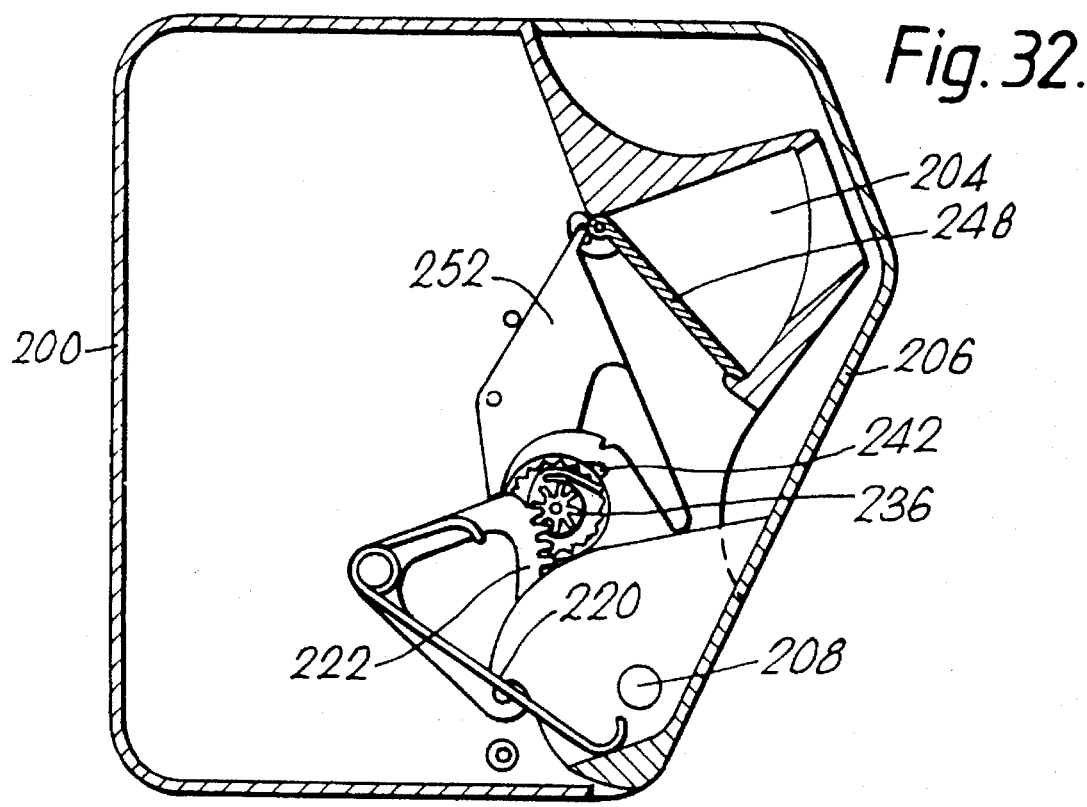
Figure 33:
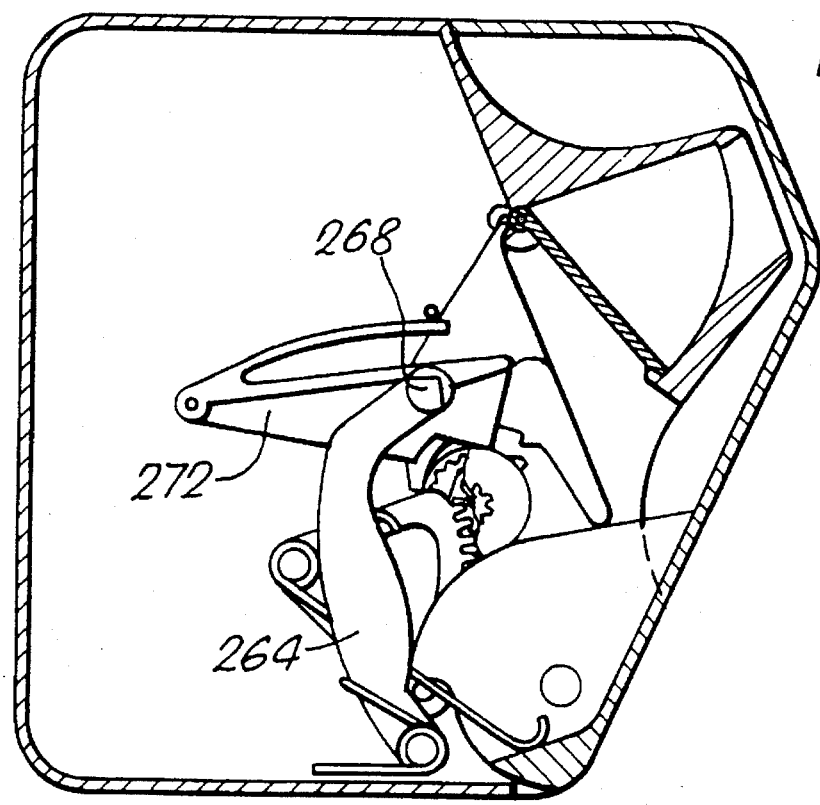

The cocking, triggering and impaction mechanism of the inhalation device is shown in FIGS. 32 and 33 and these mechanisms have substantially identical components and modes of action to those shown in FIGS. 13 to 29. Like parts are indicated by like reference numerals.

Figure 34:
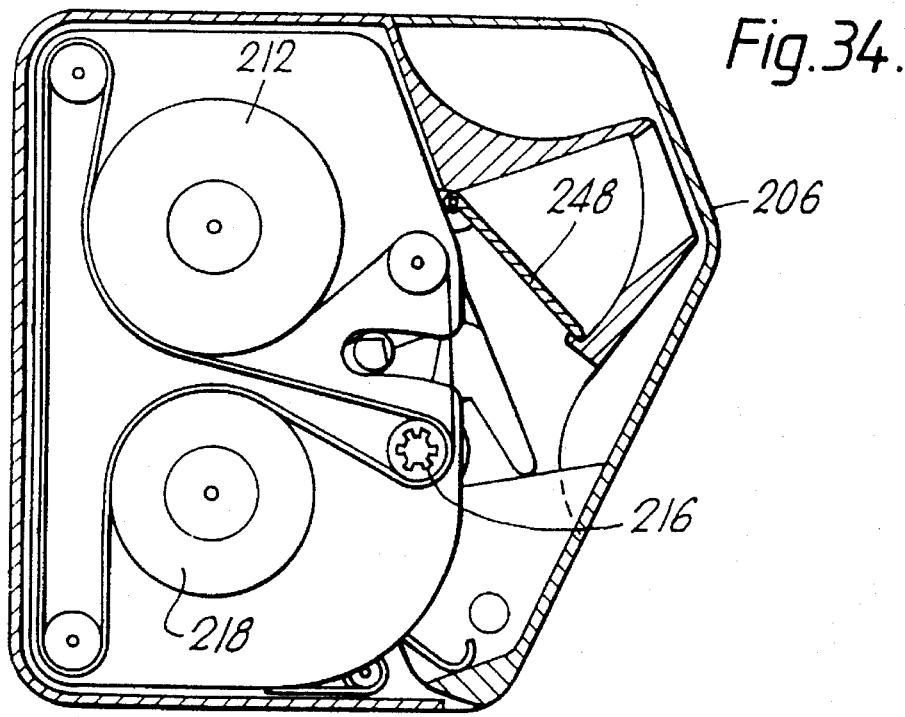
Figure 35:
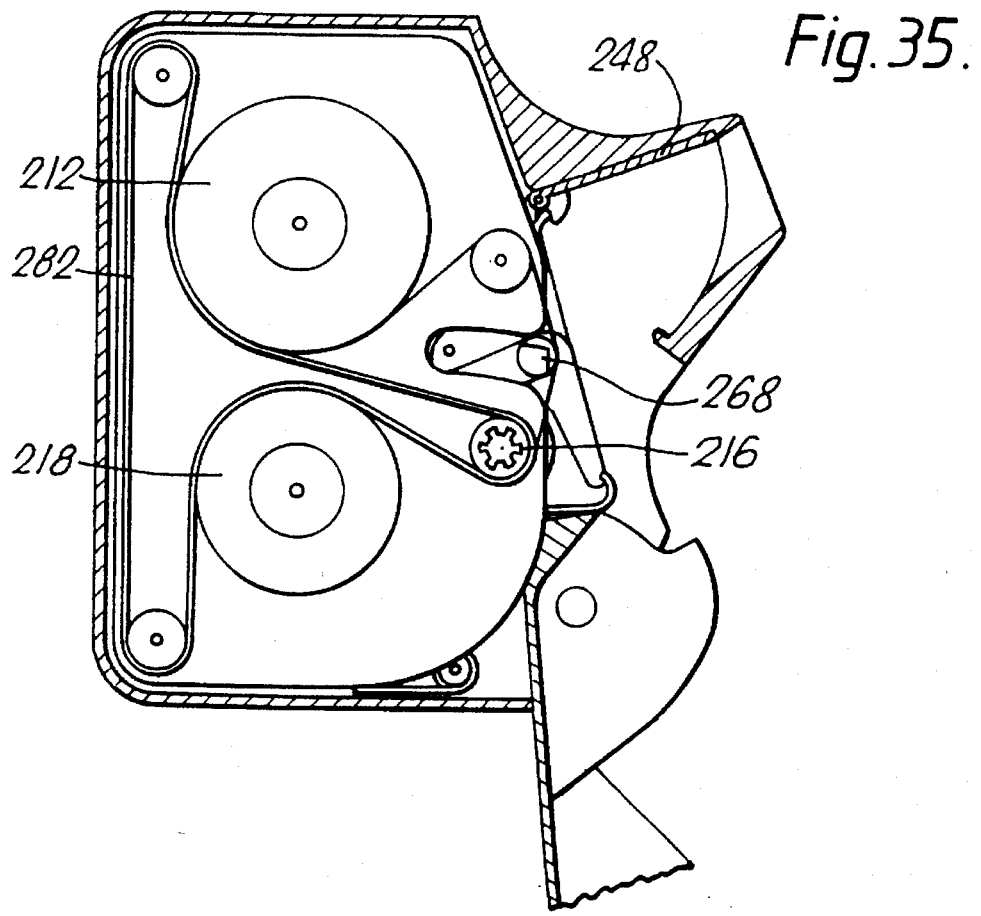

FIG. 34 shows the cassette (210) mounted in the device with the cover (206) closed and FIG. 35 shows the device in use with the impaction head (268) striking the exposed area of the elongate carrier.

Figure 36:
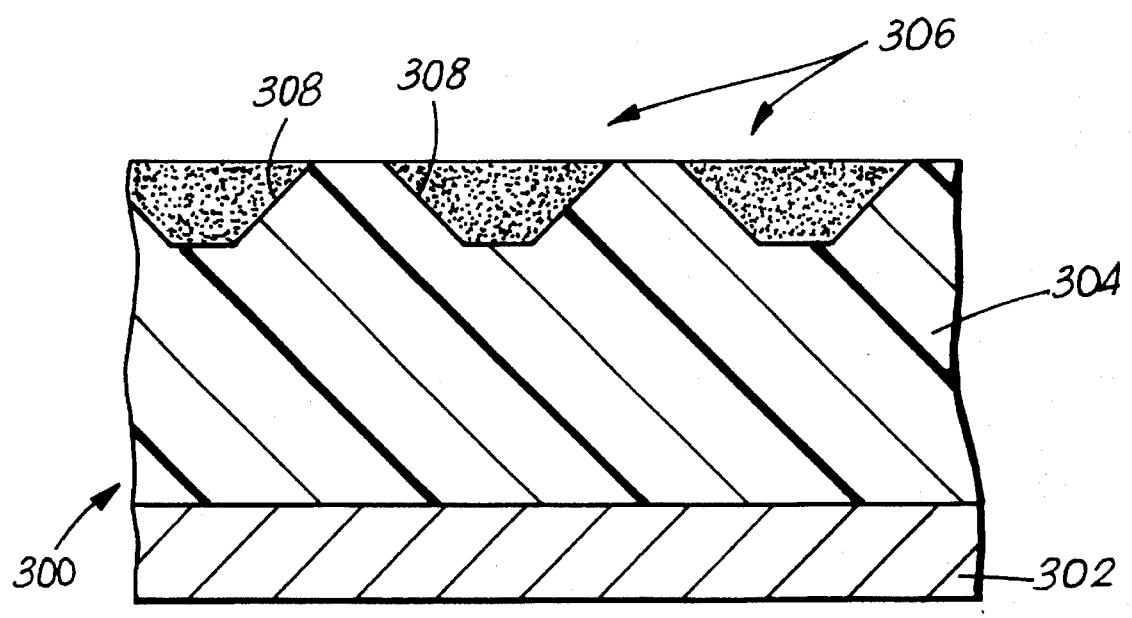
FIG. 36 is a schematic cross-sectional side view representing a micro-dimpled substrate according to one embodiment of the invention.

FIG. 36 shows one possible configuration of microdimpled substrate 300. Microdimpled substrate 300 includes an optional support layer 302 and a layer of sheet material 304. Sheet material 304 includes a plurality of microdimples 306. Microdimples 306 are preferably arranged in a regular array, as shown. The microdimples 306 may be in the form of truncated cones, as shown, or may have any other shape that is suitable for retaining powder 308.

We claim:

1. A dry powder inhalation device comprising:

a housing defining a chamber, a patient port in communication with said chamber, and one or more air inlets in communication with said chamber so that when a patient inhales through said patient port an air flow is established from the air inlets to the patient port through the chamber;

an elongate carrier disposed within said housing, preloaded with a plurality of doses of medicament, said medicament being in the form of a plurality of finely divided powder particles having a particle size in the range of from 1 to 10 μm, said finely divided powder particles being releasably retained directly on a surface of the carrier, without the presence of an adhesive between the carrier and powder particles by an attractive force between said carrier and said powder; and an advancement mechanism for exposing an area of predetermined size of the elongate carrier within the chamber so that the powder particles in said area are exposed to said air flow during inhalation and can be released from said carrier and entrained into said airflow.

2. The device of claim 1 further comprising a mechanism for applying a force to said carrier to release said powder particles from said carrier.

3. The device of claim 2 wherein said mechanism for applying a force is adapted to apply an electrical, piezoelectrical, electromagnetic or mechanical force to the carrier to vibrate the carrier.

4. The device of claim 3 wherein said mechanism for applying a force produces vibrations in the frequency range of from 5 to 50,000 Hz.

5. The device of claim 2 wherein said mechanism for applying a force comprises a member positioned to impact or strike the exposed area of the carrier.

6. The device of claim 2 wherein said mechanism for applying a force releases said powder by applying tension to said carrier.

7. The device of claim 2 wherein said mechanism for applying a force releases said powder by suddenly stopping said carrier while it is being advanced by said advancement mechanism.

8. The device of claim 2 wherein said mechanism for applying a force comprises a member positioned to scrape or brush said exposed portion of said carrier.

9. The device of claim 3 wherein said mechanism for applying a force comprises a source of compressed or liquified gas positioned to direct a flow of said gas against said exposed portion of said carrier.

10. The device of claim 2 wherein said mechanism for applying a force is actuated by inhalation by a patient.

11. The device of claim 10 further comprising a moveable vane positioned to be moved, by air flow during inhalation, from a first position to a second position in which it actuates said mechanism for applying a force.

12. The device of claim 11 wherein said moveable vane comprises a one-way valve positioned to allow passage of air from the chamber to the patient port while blocking air flow from the patient port to the chamber.

13. The device of claim 1 further comprising a tensioning element for holding said exposed portion of said carrier taut.

14. The device of claim 1 wherein said elongate carrier is provided in the form of a tape or web which is wound on a first spool and said advancement mechanism comprises a rotatable take-up spool which receives an end of said carrier and which is positioned so that rotation of the take-up spool causes a portion of the carrier to be unwound from the first spool and wound onto the take-up spool.

15. The device of claim 1 further comprising an actuator adapted to actuate the advancement mechanism after inhalation by a patient.

16. A dry powder inhalation device comprising:

a housing defining a chamber, a patient port in communication with said chamber, and one or more air inlets in communication with said chamber so that when a patient inhales through said patient port an air flow is established from the air inlets to the patient port through the chamber;

an elongate carrier disposed within said housing, having a planar surface comprising a plurality of microdepressions extending below said planar surface, said elongate carrier being preloaded with a plurality of doses of medicament, said medicament being in the form of a plurality of finely divided powder particles having a particle size in the range of from 1 to 10 μm, said finely divided powder particles being releasably retained within said microdepressions; and an advancement mechanism for exposing an area of predetermined size of the elongate carrier within the chamber so that the powder particles in said area are exposed to said air flow during inhalation and can be released from said carrier and entrained into said airflow.

17. The dry powder inhalation device of claim 16 wherein said microdepressions are selected from the group consisting of microgrooves and microdimples.

18. The dry powder inhaler of claim 16 further comprising an impactor positioned to strike a surface of said elongate carrier opposite said planar surface to cause said carrier to release said powder particles in said exposed area.

19. A dry powder inhalation device comprising:

a housing defining a chamber, a patient port in communication with said chamber, and one or more air inlets in communication with said chamber so that when a patient inhales through said patient port an air flow is established from the air inlets to the patient port through the chamber;

an elongate carrier disposed within said housing, said elongate carrier being preloaded with a plurality of doses of medicament, said medicament being in the form of a plurality of finely divided powder particles having a particle size in the range of from 1 to 10 μm, said finely divided powder particles being releasably retained directly on a powder-carrying surface of said elongate carrier without a protective capsule or coating surrounding the particles;

an advancement mechanism for exposing an area of predetermined size of the elongate carrier within the chamber so that the powder particles in said area are exposed to said air flow during inhalation and can be released from said carrier and entrained into said airflow; and a release mechanism for releasing said powder particles from said elongate carrier by applying a force to said elongate carrier, said release mechanism being positioned to avoid direct contact with said powder-carrying surface and said powder particles.

20. The dry powder inhalation device of claim 19 wherein said release mechanism comprises an impactor positioned to impact a surface of said elongate carrier opposite said powder-carrying surface.

21. A dry powder inhalation device comprising:

a housing defining a chamber, a patient port in communication with said chamber, and one or more air inlets in communication with said chamber so that when a patient inhales through said patient port an air flow is established from the air inlets to the patient port through the chamber;

an elongate carrier disposed within said housing, said elongate carrier being preloaded with a plurality of doses of medicament, said medicament being in the form of a plurality of finely divided powder particles having a particle size in the range of from 1 to 10 μm, said finely divided powder particles being releasably retained on a powder-carrying surface of said elongate carrier;

an advancement mechanism for exposing an area of predetermined size of the elongate carrier within the chamber so that the powder particles in said area are exposed to said air flow during inhalation and can be released from said carrier and entrained into said airflow; and a release mechanism for releasing said powder particles from said elongate carrier by applying a force to said elongate carrier, said release mechanism comprising an impactor positioned to strike a surface opposite said powder-carrying surface to avoid direct contact with said powder-carrying surface and said powder particles.

* * * * *